United States Patent [19]
Ojima et al.

[11] Patent Number: 5,962,744
[45] Date of Patent: Oct. 5, 1999

[54] PROCESS FOR HYDROCARBONYLATIONS IN SUPERCRITICAL CARBON DIOXIDE

[75] Inventors: Iwao Ojima, Stony Brook, N.Y.; Hisao Urata, Kanagawa, Japan

[73] Assignees: The Research Foundation of State University of New York, Stony Brook, N.Y.; Mitsubishi Chemical Corporation, Tokyo, Japan

[21] Appl. No.: 09/049,014

[22] Filed: Mar. 27, 1998

[51] Int. Cl.$^6$ .................................................. C07C 45/50
[52] U.S. Cl. ........................ 568/454; 568/451; 568/840; 568/909; 568/850; 568/882; 558/85; 556/404; 556/136
[58] Field of Search ..................... 568/454, 451, 568/840, 909, 850, 882; 558/85; 556/404, 136

[56] References Cited

U.S. PATENT DOCUMENTS

| | | | |
|---|---|---|---|
| 4,599,206 | 7/1986 | Billing et al. | 558/85 |
| 4,668,651 | 5/1987 | Billing et al. | 502/158 |
| 4,737,588 | 4/1988 | Billing et al. | 556/12 |
| 4,748,261 | 5/1988 | Billing et al. | 556/404 |
| 4,769,498 | 9/1988 | Billig et al. | 568/454 |
| 4,885,401 | 12/1989 | Billing et al. | 568/454 |
| 5,198,589 | 3/1993 | Rathke et al. | 568/454 |
| 5,235,113 | 8/1993 | Sato et al. | 568/454 |
| 5,312,996 | 5/1994 | Packett et al. | 568/454 |
| 5,360,938 | 11/1994 | Babin et al. | 568/449 |
| 5,491,266 | 2/1996 | Babin et al. | 568/449 |

OTHER PUBLICATIONS

Organometallics, vol. 14, No. 3, 1995, pp. 1510–1513, Philip G. Jessop, Takao Ikariya, and Ryoji Noyori, "Selectivity for Hydrogenation or Hydroformylation of Olefins by Hydridopentacarbonylmanganese (I) in Supercritical Carbon Dioxide".

Chemtech, pp. 719–723, (1992); Lori Boock, Ben Wu, Concetta La Marca, Michael Klein, Steve Paspek, "Reactions in Supercritical Fluids".

Science, vol. 269, pp. 1065–1069, (1995), Philip G. Jessop, Takao Ikariya, Ryoji Noyori "Homogeneous Catalysis in Supercritical Fluids".

Organometallics, 14, (1995) pp. 3876–3885, James A. Banister, Peter D. Lee and Martyn Poliakoff, "Flow Reactors for Preparative Chemistry in Supercritical Fluid Solution: Solvent–Free" Synthesis and Isolation of $Cr(CO)_5(C_2H_4)$ and $(\eta^5-C_5H_5)Mn(CO)_2(\eta-H_2)$.

Ind. Eng. Chem. Res. (1977), 36, pp. 4581–4585, Yang Guo and Aydin Akgerman, "Hydroformylation of Propylene in Supercritical Carbon Dioxide".

Organometallics (1992), 11, pp. 585–588, J. W. Rathke, R. J. Klinger and T. R. Krause, "Thermodynamics for the Hydrogenation of Dicobalt Octacarbonyl in Supercritical Carbon Dioxide".

Angew. Chem. Int. Ed. Engl., (1994), vol. 33, No. 14, Gerd Kaupp, Reactions in Supercritical Carbon Dioxide.

Angew. Chem. Int. Ed. Engl. (1997), vol. 36, No. 15, pp. 1628–1630, "Perfluoroalkyl–Substituted Arylphosphanes as Ligands for Homogeneous Catalysis in Supercritical Carbon Dioxide".

J. Am. Chem. Soc. (1996), vol. 118, pp. 344–355, Philip G. Jessop, Yi Hsiao, Takao Ikariya and Ryoji Noyori, "Homogenous Catalysis in Supercritical Fluids: Hydrogenation of Supercritical Carbon Dioxide to Formic Acid, Alkyl Formates, and Formamides".

J. Chem. Soc., Chem. Commun., (1995), pp. 707–708, Philip G. Jessop, Yi Hsiao, Takao Ikariya and Ryoji Noyori, "Methyl Formate Synthesis by Hydrogenation of Supercritical Carbon Dioxide in the Presence of Methanol".

J. Am. Chem. Soc. (1994), vol. 116, pp. 8851–8852, Philip G. Jessop, Yi Hsiao, Takao Ikariya and Ryoji Noyori "Catalytic Production of Dimethylformamide from Supercritical Carbon Dioxide".

Nature, vol. 368, (1994), pp. 231–233, P. G. Jessop, T. Ikariya and R. Noyori "Homogeneous Catalytic Hydrogenation of Supercritical Carbon Dioxide".

Organometallics, (1991), vol. 10, pp. 1350–1355, J.W. Rathke, R.J. Klingler and T. R. Krause, "Propylene Hydroformylation in Supercritical Carbon Dioxide".

Chimia, vol. 47, (1993), No. 493, Manfred T. Reetz, Werner Könen and Thomas Strack, "Supercritical Carbon Dioxide as a Reaction Medium and Reaction Partner".

Science, vol. 265, (1994), pp. 356–359, J. M. Desimone, E. E. Maury, Y.Z. Menceloglu, J.B. McClain, T. J. Romack, J.R. Combes, "Dispersion Polymerizations in Supercritical Carbon Dioxide".

Science, vol. 257, (1992), pp. 945–947, J.M. DeSimone, Zihibin Guan and C. S. Elsbernd, "Synthesis of Fluoropolymers in Supercritical Carbon Dioxide".

J. Am. Chem. Soc., (1995), vol. 117, pp. 8277–8278, Mark J. Burk, Shaoguang Feng, Michael F. Gross and William Tumas "Asymmetric Catalytic Hydrogenation Reactions in Supercritical Carbon Dioxide".

Science, (1994), vol. 263, pp. 203–205, James M. Tanko and Joseph F. Blackert "Free–Radical Side–Cain Bromination of Alkylaromatics in Supercritical Carbon Dioxide".

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A process comprising subjecting at least one compound containing at least one carbon—carbon double bond or at least one carbon—carbon triple bond, hydrogen and carbon monoxide, to a hydrocarbonylation reaction in supercritical carbon dioxide, in the presence of a Group VIII transition metal catalyst precursor, and a phosphite ligand.

35 Claims, No Drawings

PROCESS FOR HYDROCARBONYLATIONS IN SUPERCRITICAL CARBON DIOXIDE

The invention disclosed herein was in part supported by a grant from the National Science Foundation (CHE 9710504). The United States government may have an interest therein.

FIELD OF THE INVENTION

The present invention relates to new process for carbonylations using supercritical carbon dioxide as the specific reaction medium, which is environmentally benign and non-flammable.

BACKGROUND OF THE INVENTION

The industrial processes for production of commodity chemicals and specialty chemicals often use transition metal catalyzed reactions, which are performed in organic solvents. However in recent years, these organic solvents are under close scrutiny with regard to the increasing environmental regulatory restrictions because of their intrinsic toxicity as well as the safety hazard due to their flammable nature. The use of water is a solution to these problems. However, water is not a friendly solvent for most transition metal catalysts because of their solubility in water as well as their sensitivity to water. Accordingly, the use of supercritical fluids, especially supercritical carbon dioxide provides an attractive solution.

It has been shown that supercritical fluids are useful as media for extraction and chromatography in academic laboratories as well as industrial processes [P. G. Jessop, T. Ikariya, and R. Noyori, *Science*, 269, 1065–1069 (1995)]. Supercritical fluids also provide advantages as unique reaction media, e.g., the density, polarity, viscosity, diffusivity, and solvating ability of supercritical fluids can be dramatically changed by small variation of the pressure and/or temperature. [L. Boock, B. Wu, C. LaMarca, M. Klein, and S. Paspek, *CHEMTECH*, 719–723 (1992); G. Kaupp, *Angew. Chem. Int. Ed. Engl.*, 33, 1452–1455 (1994)]. It has recently been demonstrated that increase in reaction rate and change in selectivity can be achieved by replacing conventional organic solvents by supercritical fluids such as supercritical carbon dioxide (scCO$_2$) and supercritical water (scH$_2$O). [P. G. Jessop, T. Ikariya, and R. Noyori, *Science*, 269, 1065–1069 (1995); J. A. Banister, P. D. Lee, and M. Poliakoff, *Organometallics*, 14, 3876–3885 (1995); S. Kainz, D. Koch, W. Baumann, and W. Leitner, *Angew. Chem., Int. Ed. Engl.*, 36, 1628–1630 (1997); J. W. Rathke, R. J. Klingler, and T. R. Krause, *Organometallics*, 11, 585 (1992)].

As a medium for organic synthetic reactions and homogeneous catalysis, scCO$_2$ appears to be most suitable because of its mild critical point, i.e., $T_c=31°$ C., $P_c=72.9$ atm. In fact, free radical reaction, polymerization, hydrogenation, hydroformylation, and carboxylation reactions have been successfully carried out in scCO$_2$.[S. Kainz, D. Koch, W. Baumann, and W. Leitner, *Angew. Chem., Int. Ed. Engl.*, 36, 1628–1630 (1997); J. W. Rathke, R. J. Klingler, and T. R. Krause, *Organometallics*, 11, 585 (1992); Y. Guo, and A. Akgerman, *Ind. Eng. Chem. Res.*, 36, 4581–4585 (1997); P. G. Jessop, Y. Hsiao, T. Ikariya, and R. Noyori, *J. Am. Chem. Soc.*, 118, 344–355 (1996); P. G. Jessop, T. Ikariya, and R. Noyori, *Organometallics*, 14, 1510–1513 (1995); P. G. Jessop, Y. Hsiao, T. Ikariya, and R. Noyori, *J. Chem. Soc., Chem. Commun.*, 707–708 (1995); P. G. Jessop, Y. Hsiao, T. Ikariya, and R. Noyori, *J. Am. Chem. Soc.*, 116, 8851–8852 (1994); P. G. Jessop, T. Ikariya, and R. Noyori, *Nature*, 368, 231–233 (1994); J. W. Rathke, and R. J. Klingler, U.S. Pat. No. 5,198,589 (1993); J. W. Rathke, R. J. Klingler, and T. R. Krause, *Organometallics*, 10, 1350–1355 (1991); M. T. Reetz, W. Konen, and T. Strack, *Chimia*, 47, 493 (1993); J. M. DeSimone, E. E. Maury, Y. Z. Menceloglu, J. B. McClain, T. J. Romack, and J. R. Combes, *Science*, 265, 356–359 (1994); J. M. DeSimone, Z. Guan, and C. S. Elsbernd, *Science*, 257, 945–947 (1992); M. J. Burk, S. Feng, M. F. Gross, and W. Tumas, *J. Am. Chem. Soc.*, 117, 8277–8278 (1995)].

It is anticipated that increased reaction rate and selectivity may result from the following characteristics of scCO$_2$ in homogeneous catalysis: (i) local clustering of reactants and a very large activation volume near the critical point, (ii) weakened solvation around reactive species, (iii) rapid diffusion of solute molecules, (iv) high solubility of gases, (v) disfavoring the cage effects in radical processes.[P. G. Jessop, T. Ikariya, and R. Noyori, *Science*, 269, 1065–1069 (1995)] In addition to these characteristics, scCO$_2$ serves as environmentally benign, non-flammable reaction medium that does not cause solvent residues and waste originated from conventional organic solvents. The separation of the product(s), catalyst, and reactant(s) can be easily performed through selective precipitation.[P. G. Jessop, T. Ikariya, and R. Noyori, *Science*, 269, 1065–1069 (1995)].

In spite of the recent recognition of these very useful features of scCO$_2$, only a very limited number of homogeneous catalytic reactions have been investigated using scCO$_2$ as the medium.[[P. G. Jessop, T. Ikariya, and R. Noyori, *Science*, 269, 1065–1069 (1995); J. W. Rathke, R. J. Klingler, and T. R. Krause, *Organometallics*, 10, 1350–1355 (1991); M. T. Reetz, W. Konen, and T. Strack, *Chimia*, 47, 493 (1993); M. J. Burk, S. Feng, M. F. Gross, and W. Tumas, *J. Am. Chem. Soc*, 117, 8277–8278 (1995)].

Hydroformylation of propene catalyzed by Co$_2$(CO)$_8$ in scCO$_2$ has been studied [J. W. Rathke, R. J. Klingler, and T. R. Krause, *Organometallics*, 10, 1350–1355 (1991); Y. Guo, and A. Akgerman, *Ind. Eng. Chem. Res.*, 36, 4581–4585 (1997)]. Hydroformylation of olefins catalyzed by Group VIII metal catalysts, which may be complexed with phosphine ligands, in scCO$_2$ have been patented [J. W. Rathke and R. J. Klingler, U.S. Pat. No. 5,198,589 (1993)]. Hydroformylation of alkenes catalyzed by HMn(CO)$_5$ was also studied [P. G. Jessop, T. Ikariya, and R. Noyori, *Organometallics*, 14, 1510–1513 (1995)]. Hydroformylation of 1-octene catalyzed by a rhodium complex with tris(m-perfluoroalkyl-substituted phenyl)phosphine, which results in a catalyst that is substantially more soluble in supercritical carbon dioxide than those using conventional non-fluorinated phosphine ligands. was reported [S. Kainz, D. Koch, W. Baumann, and W. Leitner, *Angew. Chem., Int. Ed. Engl.*, 36, 1628–1630 (1997)].

The cobalt-catalyzed processes need high pressure and high temperature in a manner similar to the conventional cobalt-catalyzed hydroformylation process in organic solvents. The manganese-catalyzed process is not practical in terms of efficacy. The rhodium-catalyzed process using tris(m-perfluoroalkyl-substituted phenyl)phosphine has been carried out at 220 atm total pressure and the pressure of hydrogen and carbon monoxide (1:1) at ambient temperature is 60 atm, which are still quite high pressures.

One of the objects of the present invention is to provide carbonylation reaction processes including hydroformylation and cyclohydrocarbonylation of functionalized and unfunctionalized alkenes, alkadienes, and alkynes catalyzed by Group VIII transition metal complexes in scCO$_2$ that are different from and/or improved over the prior art. Another object is to provide such processes that can be carried out at lower pressures than the prior art. Another object is to provide such processes that employ a ligand that does not need a special modification such as introducing perfluoroalkyl group(s) to provide adequate solubility of the catalyst in supercritical carbon dioxide. Applicants have discovered that these objects can be achieved by using a phosphite ligand in combination with a Group VIII transition metal catalyst or catalyst precursor.

SUMMARY OF THE INVENTION

The present invention comprises a process comprising subjecting at least one compound containing at least one carbon—carbon double bond or at least one carbon—carbon triple bond, hydrogen and carbon monoxide, to a hydrocarbonylation reaction in supercritical carbon dioxide, in the presence of a Group VIII transition metal catalyst precursor, and a phosphite ligand.

The processes of the present invention using Group VIII transition metal complexes with phosphite ligands in supercritical carbon dioxide require only low pressures of a mixture of hydrogen and carbon monoxide, and thus the total pressure of the process can be less than 100 atm. Also, functionalized unsaturated substrates can be used in the process of this invention, which provide useful intermediates for pharmaceuticals and agrochemicals through hydrocarbonylations.

DETAILED DESCRIPTION OF THE INVENTION

The processes of this invention include hydrocarbonylations such as hydroformylation and cyclohydrocarbonylation of at least one compound containing at least one carbon—carbon double bond or at least one carbon—carbon triple bond (unsaturated compound), preferably alkenes, alkynes, and dienes, catalyzed by Group VIII transition metal complexes with phosphite ligands in supercritical carbon dioxide (scCO$_2$).

There is no limitation on the unsaturated compound, so long as it is capable of undergoing the carbonylation reaction. Preferred unsaturated compounds are alkenes, alkynes, dienes, and mixtures thereof. These compounds can be unsubstituted or substituted with functional or substituent groups. The functional or substituent groups are not limited, and include all such groups that survive the carbonylation reaction intact. In the disclosure that follows and in the appended claims, these functional or substituent groups are disclosed and recited as "nonreactive", because they do not enter into the carbonylation reaction.

The alkenes are selected from the group consisting of 1-alkenes and internal alkenes. The alkynes are selected from. the group consisting of 1-alkynes and internal alkynes; wherein the alkenes, alkynes and the dienes are acyclic or cyclic; wherein the alkenes, alkynes, and dienes are linear or branched, and wherein the alkenes, alkynes, and dienes are unsubstituted or substituted with one or more nonreactive substituents.

Examples of nonreactive substituents include hydroxy, alkoxy, aryloxy, formyl, oxo, hydroxycarbonyl and/or its derivative, amino, amido, imido, carbamoyl, ureido and/or its derivative, cyano, nitro, alkoxycarbonyloxy, aryloxycarbonyloxy, mercapto, alkylthio, arylthio, thioxo, hydroxy(thiocarbonyl) and/or its derivative, mercaptocarbonyl and/or its derivative, mercapto(thiocarbonyl) and/or its derivative, sulfinyl, sulfonyl, phosphino, (phosphino)oxy, phosphoryl, phosphonamido, phosphonthioamido, trisubstituted silyl, trisubstituted stannyl, and disubstituted boryl.

Preferred alkenes include straight chain or branched 1-alkene of 2–20 carbons, straight chain or branched internal alkenes of 4–20 carbons, cycloalkenes of 3–20 carbons, unsubstituted or substituted alkenylarenes of 8–30 carbons, unsubstituted or substituted alkenylheteroaromatic compounds of 5–30 carbons, unsubstituted or substituted alkenylcycloalkanes of 5–30 carbons, unsubstituted or substituted alkenylcyclic compounds including one or more nitrogen atoms of 4–30 carbons, unsubstituted or substituted alkenylcyclic compounds including one or more oxygen atoms of 4–30 carbons, unsubstituted or substituted alkenylcyclic compounds including one or more sulfur atoms of 4–30 carbons, and unsubstituted or substituted alkenylcyclic compounds including one or more phosphorus atoms of 4–30 carbons.

Preferred substituted alkenes include unsubstituted and substituted allylic amines, unsubstituted and substituted allylic amides, unsubstituted and substituted allylic carbamates, unsubstituted and substituted allylic sulfonamides, unsubstituted and substituted allylic phosphonamides, unsubstituted and substituted 3-butenylamines, unsubstituted and substituted 3-butenylamides, unsubstituted and substituted 3-butenylcarbamates, unsubstituted and substituted 3-butenylsulfonamides, unsubstituted and substituted 3-butenylphosphonamides, unsubstituted and substituted 4-pentenylamines, unsubstituted and substituted 4-pentenylamides, unsubstituted and substituted 4-pentenylcarbamates, unsubstituted and substituted 4-pentenylsulfonamides, and unsubstituted and substituted 4-pentenylphosphonamides.

Preferred substituted dienes include unsubstituted and substituted 3-amino-1,4-pentadiene, unsubstituted and substituted 3-amino-1,5-hexadiene, unsubstituted and substituted 3-amino-1,6-heptadiene, unsubstituted and substituted 4-amino-1,6-heptadiene, unsubstituted and substituted 4-amino-1,7-octadiene, 5-amino-1,8-nonadiene, unsubstituted and substituted 3-hydroxy-1,4-pentadiene, unsubstituted and substituted 3-hydroxy-1,5-hexadiene, unsubstituted and substituted 3-hydroxy-1,6-heptadiene, unsubstituted and substituted 4-hydroxy-1,6-heptadiene, unsubstituted and substituted 4-hydroxy-1,7-octadiene, 5-hydroxy-1,8-nonadiene, unsubstituted and substituted 3-mercapto-1,4-pentadiene, unsubstituted and substituted 3-mercapto-1,5-hexadiene, unsubstituted and substituted 3-mercapto-1,6-heptadiene, unsubstituted and substituted 4-mercapto-1,6-heptadiene, unsubstituted and substituted 4-mercapto-1,7-octadiene, 5-mercapto-1,8-nonadiene.

There is no limitation on Group VIII transition metal catalyst precursors used in this invention, and a variety of Group VIII transition metal catalyst precursors, alone or mixtures thereof, known for hydroformylation can be used in these processes. The Group VIII transition metal compound as the catalyst or its precursor for the hydrocarbonylation reaction, may, for example, be a hydride, a halide, an organic salt, an inorganic salt, an oxide, a carbonyl compound, an amine compound, an olefin-coordinated compound, a phosphine-coordinated compound or a phosphite-coordinated compound.

The Group VIII transition metal includes rhodium, platinum, ruthenium, cobalt, iridium, osmium, and palladium.

Examples of the Group VIII metal compounds include ruthenium compounds such as Ru$_3$(CO)$_{12}$, Ru(NO$_3$)$_3$, RuCl$_3$(Ph$_3$P)$_3$ and Ru(acac)$_3$; palladium compounds such as PdCl$_2$, Pd(OAc)$_2$, Pd(acac)$_2$, PdCl$_2$(COD) and PdCl$_2$(Ph$_3$P)$_2$; osmium compounds such as Os$_3$(CO)$_{12}$ and OsCl$_3$; iridium compounds such as Ir$_4$(CO)$_{12}$ and IrSO$_4$; platinum compounds such as K$_2$PtCl$_4$, PtCl$_2$(PhCN)$_2$ and Na$_2$PtCl$_6$.6H$_2$O; cobalt compounds such as CoCl$_2$, Co(NO$_3$)$_2$, Co(OAc)$_2$ and Co$_2$(CO)$_8$; and rhodium compounds such as RhCl$_3$, Rh(NO$_3$)$_3$, Rh(OAc)$_3$, Rh$_2$O$_3$, Rh(acac)(CO)$_2$, [Rh(OAc)(COD)]$_2$, Rh$_4$(CO)$_{12}$, Rh$_6$(CO)$_{16}$, HRh(CO)(PPh$_3$)$_3$, [Rh(OAc)(CO)$_2$]$_2$, [Rh($\mu$-S(t-Bu))(CO)$_2$]$_2$, [RhCl(COD)]$_2$, [Rh(CH$_2$=CH$_2$)$_2$Cl]$_2$, [Rh(norbornadiene)Cl]$_2$, [Rh(CO)$_2$Cl]$_2$, wherein acac represents an acetylacetonate group, Ac an acetyl group, COD 1,5-cyclooctadiene, Ph a phenyl group and t-Bu a t-butyl group. However, the Group VIII transition metal compounds are not limited to such specific examples.

In the process of the present invention, the phosphite compound may be used to form a complex with the Group VIII transition metal compound described above. The Group VIII transition metal complex containing the phosphite compound can readily be prepared by a conventional method for forming a complex from a metal compound and the phosphite compound. In some cases, the metal compound and the phosphite compound may be supplied to the reaction vessel to form the complex in situ.

The amount of the Group VIII transition metal compound is not particularly limited, but there is a limit from the viewpoint of the catalytic activity and the economical feasibility. It is usually selected in a manner that the concentration in the reaction vessel is 1×10$^{-9}$ M~1×10$^{-3}$ M, preferably from 1×10$^{-8}$ M~1×10$^{-4}$ M as calculated as the metal.

There is no limitation on the phosphite ligand used in this invention. The phosphite compound of the present invention is preferably selected from the formulae (I) to (IV), below. These ligands are generally known and/or can be prepared routinely by persons skilled in the art, and some of these ligands have been disclosed for hydroformylation reactions, but none for use with a supercritical carbon dioxide medium. See R. L. Pruett and J. A. Smith, *J. Org. Chem.*, 34, 327 (1969) for formula (I); U.S. Pat. Nos. 4,599,206 and 4,737,588 for formula (I-1); DE19717359-A1, which is the published equivalent of U.S. patent application Ser. No. 08/845,835 for formula (II); U.S. Pat. No. 4,748,261 and U.S. Pat. No. 4,885,401 for formula (II-1); U.S. Pat. No. 4,668,651 and J. R. Johnson, G. D. Cuny, and S. L. Buchwald, *Angew. Chem. Int. Ed. Engl.*, 34, 1760 (1995) for formula (II-2); N. Sakai, S. Mano, K. Nozaki, and H. Takaya, *J. Am. Chem. Soc.* 115, 7033–7034 (1993) for formula (III-1) and (IV-1). See also U.S. Pat. No. 5,491,266, U.S. Pat. No. 5,360,938, U.S. Pat. No. 5,312,996 and U.S. Pat. No. 5,235,113.

P(OR$^1$)(OR$^2$)(OR$^3$) (I)

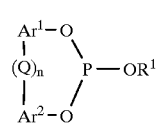 (I-1)

 (II)

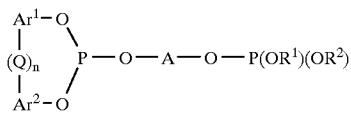 (II-1)

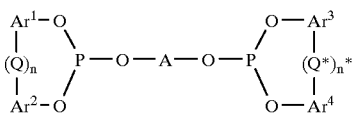 (II-2)

(R$^1$O)(R$^2$O)P—O—A—O—P(R$^3$)(R$^4$) (III)

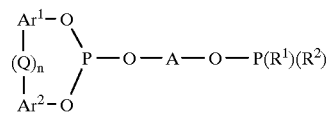 (III-1)

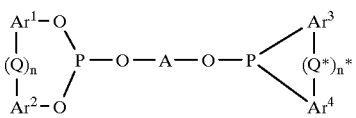 (III-2)

(R$^1$O)(R$^2$O)P—O—A—O—P(R$^3$)(R$^4$) (IV)

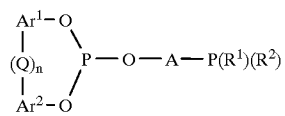 (IV-1)

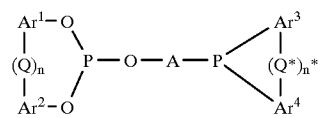 (IV-2)

In the formula (I), each R$^1$, R$^2$ or R$^3$ independently represents a C1–20 linear, branched or cyclic alkyl group such as methyl, ethyl, butyl, tertiary-butyl, octyl, and cyclohexyl groups, a C6–C20 aryl group, such as phenyl, tolyl, xylyl, naphthalenyl, anthracenyl, phenanthrenyl, pyrenyl, and benzopyrenyl groups or a C3–C20 heteroaromatic group such as imidazolyl, furyl, thienyl, pyrrolyl, pyridyl, benzofuryl, dibenzofury, indolyl, and dibenzopyrrolyl groups, which may have one or more substituents.

As a substituent, a C1–C20 linear or branched alkyl group such as methyl, ethyl, propyl, isopropyl, butyl, tert-butyl, and nonyl groups, a cycloalkyl group such as cyclopropyl, cyclohexyl, and cyclooctyl groups, an alkoxy group such as methoxy, ethoxy, isopropoxy, tert-butoxy, and cyclohexyloxy groups, an aryl group such as phenyl, tolyl, 1-naphthyl, and 2-naphthyl groups, an aryloxy group such as phenoxy, tolyloxy, xylyloxy, and naphthyloxy groups, an aralkyl group such as benzyl, tolylmethyl, 1-phenylethyl, and naphthylmethyl groups, a nitro group, a cyano group, an ester group, a perfluoroalkyl group such as trifluoromethyl, pentafluoroethyl, heptafluoropropyl, nonafluorobutyl, and heptadecafluorooctyl groups, an amide group, trialkylsilyl group or halogen atom are exemplified.

Examples of the phosphites of the formula (I) are (BuO)$_3$P and those shown below:

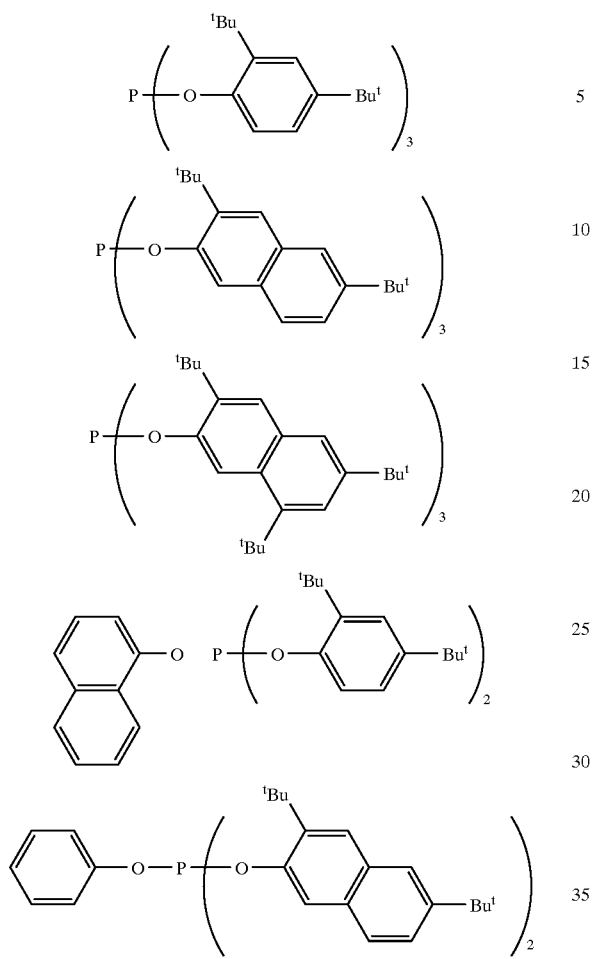

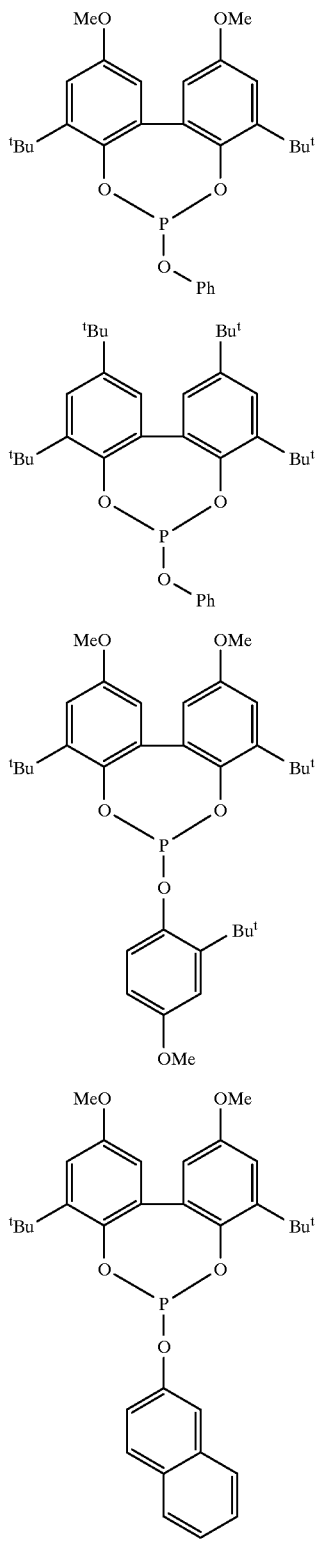

In the formula (I-1), each $Ar^1$ or $Ar^2$ represents a non-substituted or substituted arylene group such as 1,2-phenylene and 1,2-naphthylene wherein as a substituent, methyl, ethyl, propyl, isopropyl, butyl, tert-butyl, octyl, cyclohexyl, methoxy, ethoxy, tert-butoxy, phenyl, tolyl, benzyl, acetyl, benzoyl, cyano, nitro, trimethylsilyl group, and halogen atom are exemplified;

Q represents a —$CR^5R^6$, —O—, —S—, —$NR^7$, —$SiR^8R^9$ or —CO— group as a linker group wherein each $R^5$ to $R^9$ independently represents a hydrogen atom, C1–C 12 alkyl group or aryl group, and n represents 0 or 1.

Examples of the phosphites of the formula (I-1) are shown below, wherein Ph in this formula, and in subsequent formulae, represents phenyl:

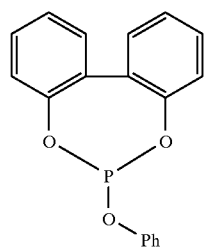

-continued
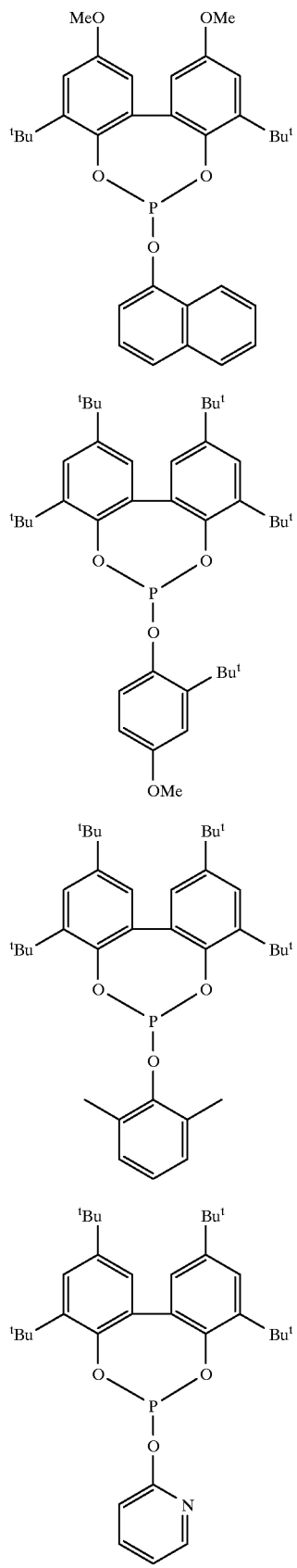
-continued
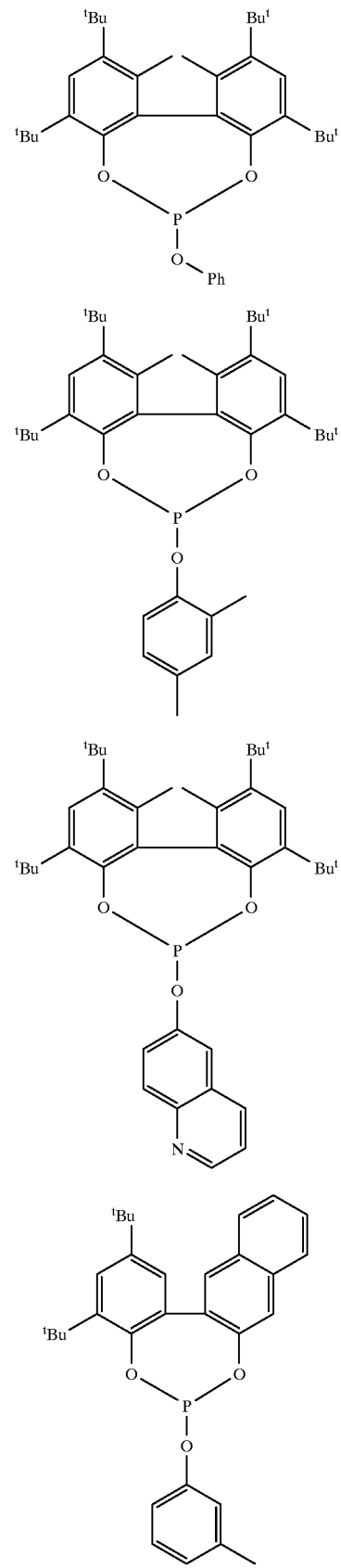

-continued

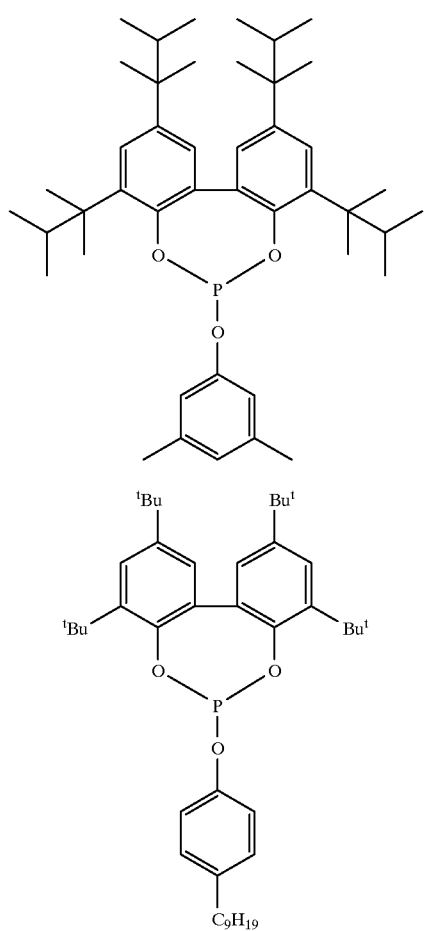

In the formula (II), A represents a C2–C12 linear, branched or cyclic alkylene group, a C6–10 arylene group or a C12–C20 bisarylene group, which may have one or more substituents.

As a substituent, a C1–C20 linear or branched alkyl group such as methyl, ethyl, propyl, isopropyl, butyl, tert-butyl, and nonyl groups, a cycloalkyl group such as cyclopropyl, cyclohexyl, and cyclooctyl groups, an alkoxy group such as methoxy, ethoxy, isopropoxy, tert-butoxy and cyclohexyloxy groups, an aryl group such as phenyl, tolyl, 1-naphthyl, and 2-naphthyl groups, an aryloxy group such as phenoxy, tolyloxy, xylyloxy, and naphthyloxy groups, an aralkyl group such as benzyl, tolylmethyl, 1-phenylethyl, and naphthylmethyl groups, a nitro group, a cyano group, an ester group, a perfluoroalkyl group such as trifluoromethyl, pentafluoroethyl, heptafluoropropyl, nonafluorobutyl, and heptadecafluorooctyl groups, an amide group, trialkylsilyl group or halogen atom are exemplified.

As an alkylene group, 1,2-ethylene, 1,3-propylene, 1,4-butylene, 2,4-pentylene, 1,2-cyclohexylene, 1,3-cyclohexylene, or 4-methyl-1,3-cyclohexylene group are exemplified.

As an arylene group, a 1,2-phenylene, 1,3-phenylene, 1,4-phenylene, 2,5-dimethyl-1,4-phenylene, 1,2-naphthylene, 1,4-naphthylene, 2,3-naphthylene, 6,8-di-tert-butyl-1,4-naphthylene or 5,6,7,8-tetrahydro-1,4-naphthylene group are exemplified.

As an bisarylene group, a 1,1'-biphenyl-2,2'-diyl, 3,3',5,5'-tetra-tert-butyl-1,1'-biphenyl-2,2'-diyl, 3,3'-di-tert-butyl-5,5'-dimethyl-1,1'-biphenyl-2,2'-diyl, 3,3',5,5'-tetra-tert-butyl-6,6'-dimethyl-1,'-biphenyl-2,2'-diyl, 3,3',5,5'-tetra-tert-pentyl-1,1 '-biphenyl-2,2'-diyl, 3,3',5,5'-tetra-tert-hexyl-1,1'-biphenyl-2,2'-diyl, 3,3'-di-tert-butyl-5,5'-dimethoxy-1,1'-biphenyl-2,2'-diyl, 3,3'-di-tert-butyl-5,5'-diethoxy-1,1'-biphenyl-2,2'-diyl, 3,3'-di-tert-butyl-5,5'-di-tert-butoxy-1,1'-biphenyl-2,2'-diyl, 3,3',5,5'-tetra-cyclohexyl-1,1'-biphenyl-2,2'-diyl, 1,1'-binaphthyl-2,2'-diyl, 3,3',6,6'-tetra-tert-butyl-1,1'-binaphthyl-3,3'-binaphthyl-2,2'-diyl or 1,1',7,7'-tetra-tert-butyl-3,3'-binaphthyl-2,2'-diyl group are exemplified.

In the formula (II), $R^4$ is the same as that defined above for each $R^1$, $R^2$, or $R^3$.

Examples of the phosphites of the formula (II) are shown below:

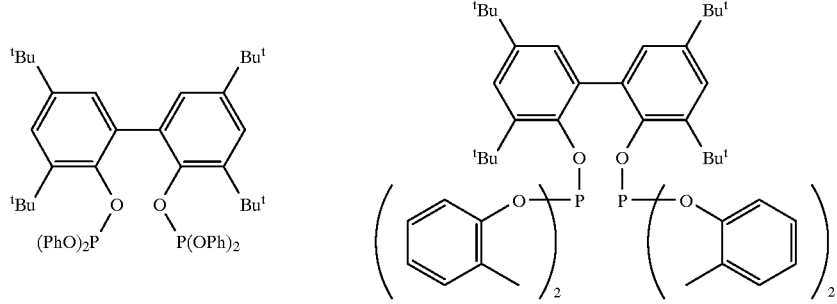

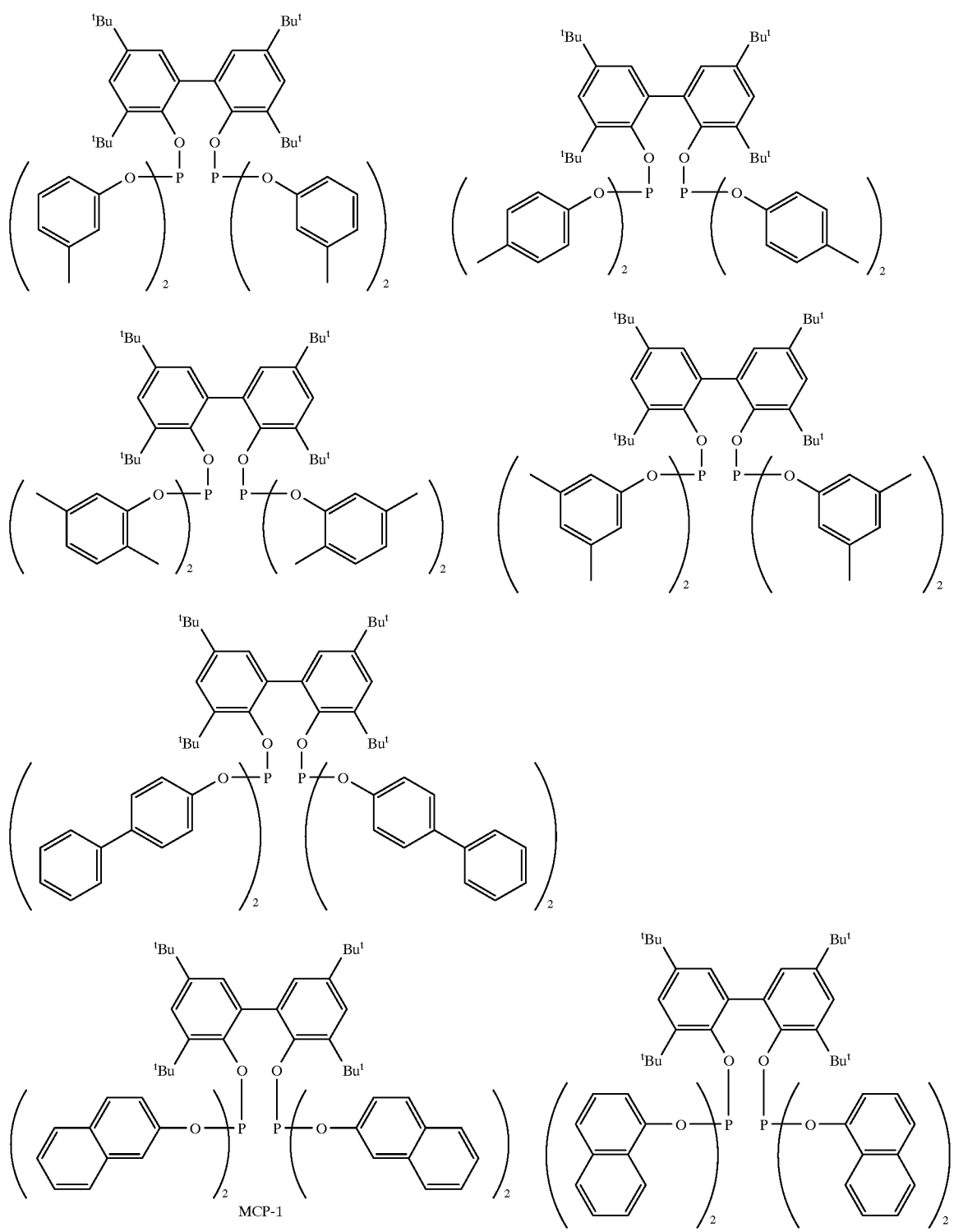

-continued
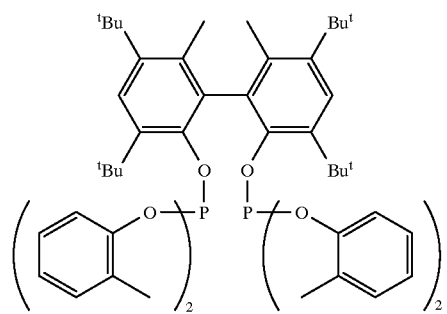
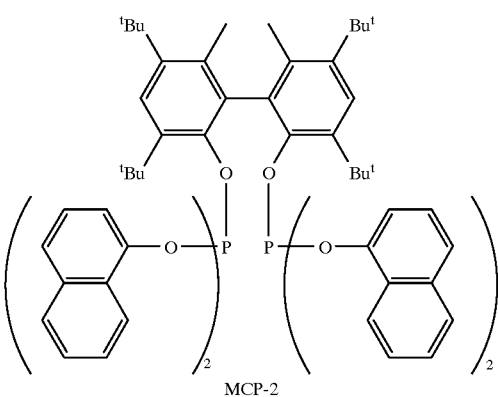
MCP-2
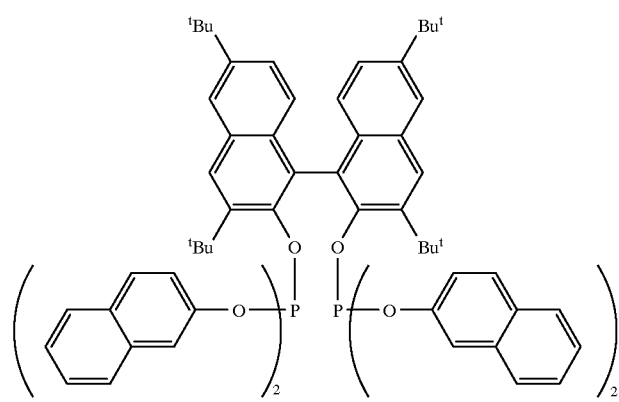
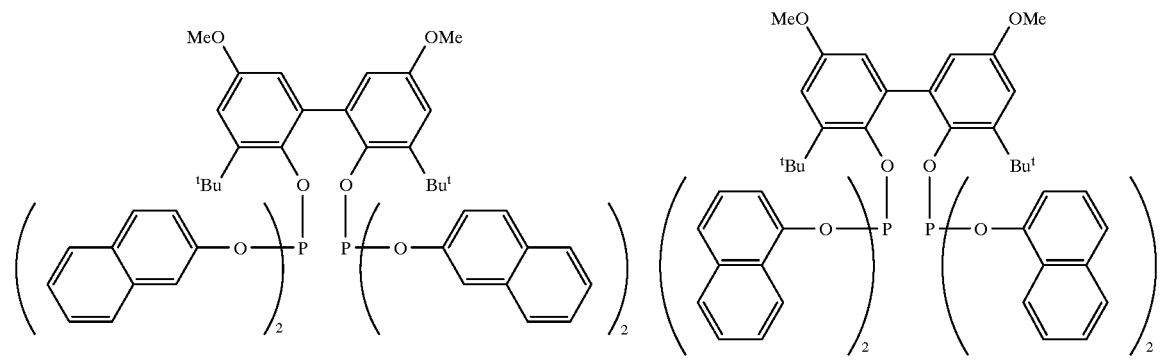
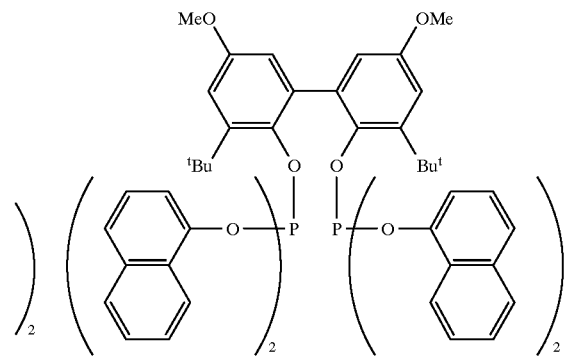
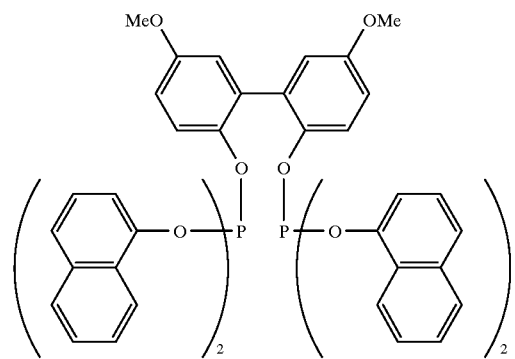
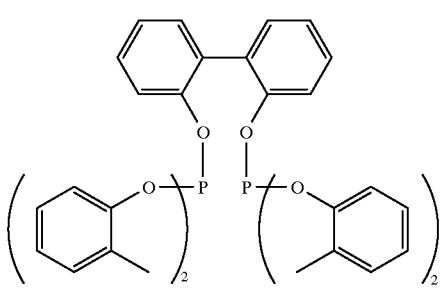

17 18
-continued
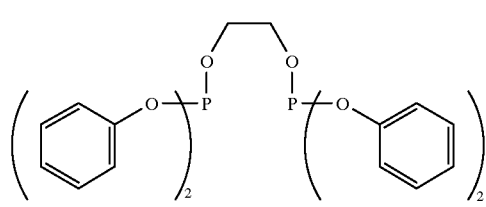
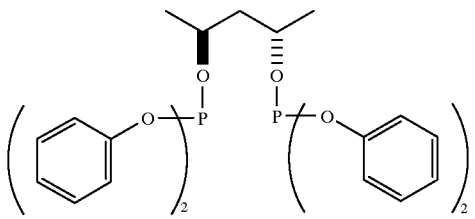
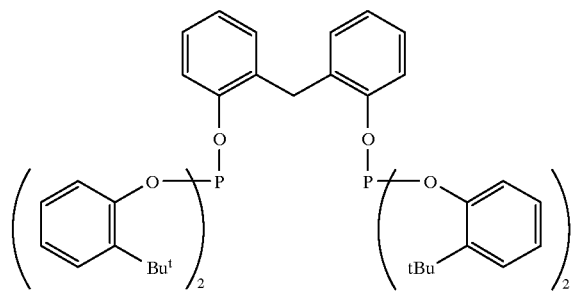
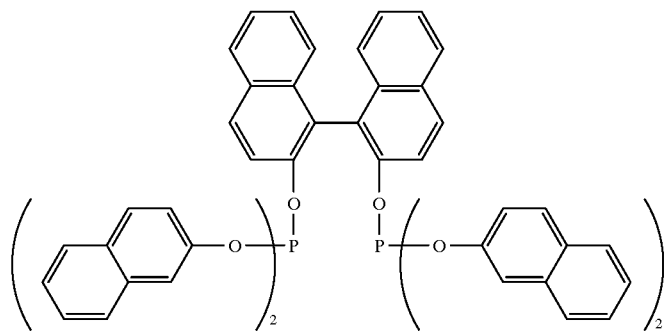
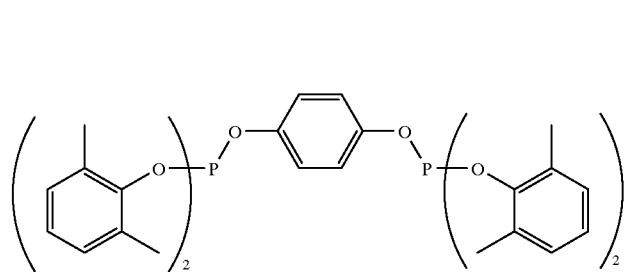
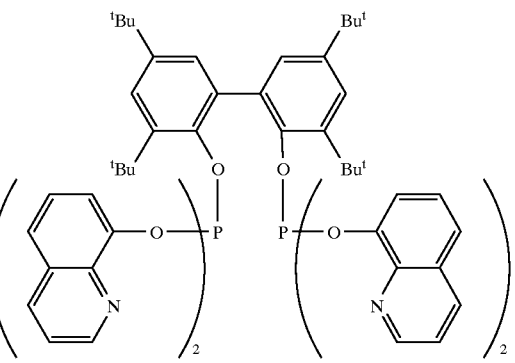
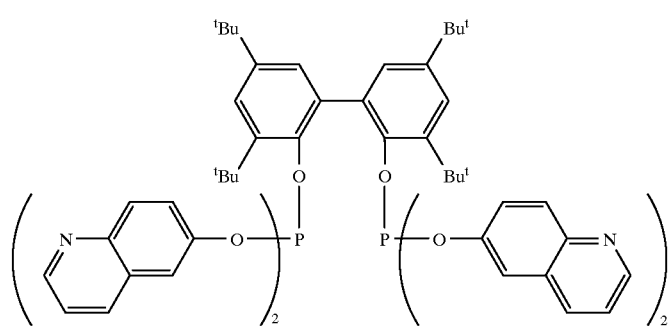

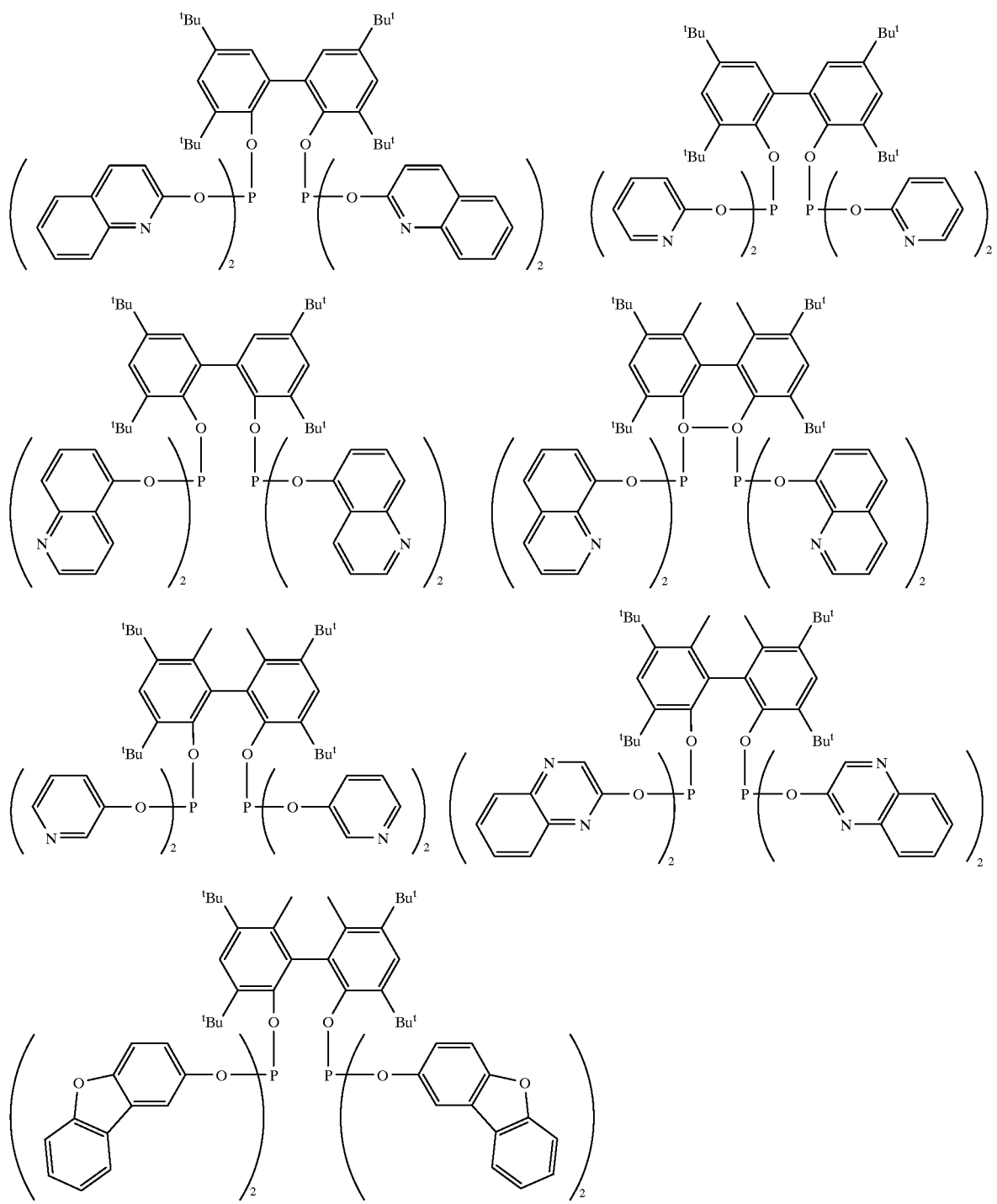

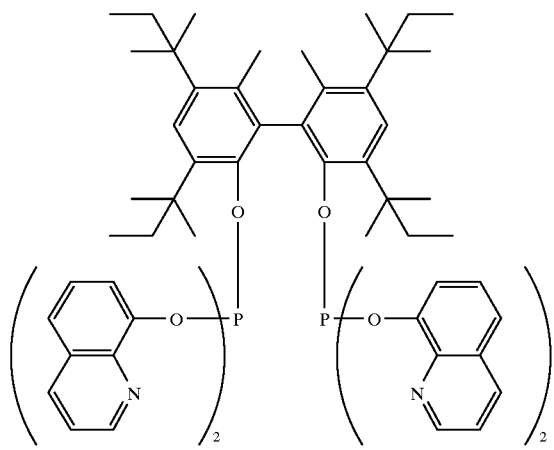
In the formulae (II-1) and (II-2), $Ar^1$, $Ar^2$, Q, and n have been defined above.
Examples of the phosphites of the formula (II-1) are shown below:
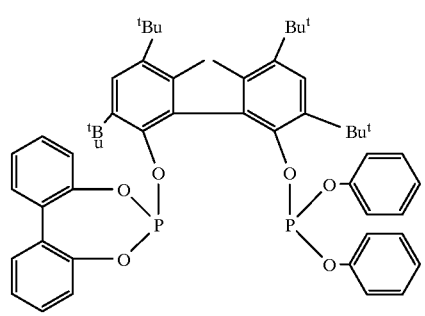
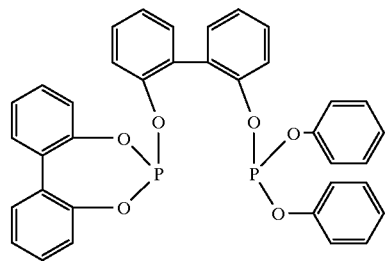
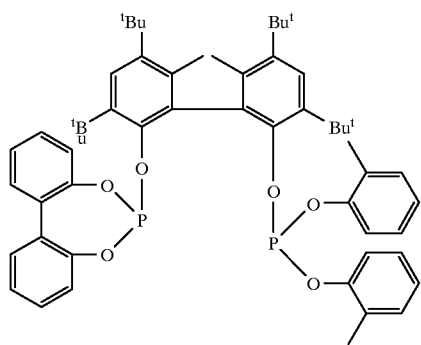
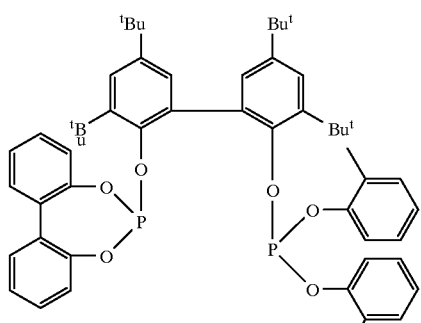
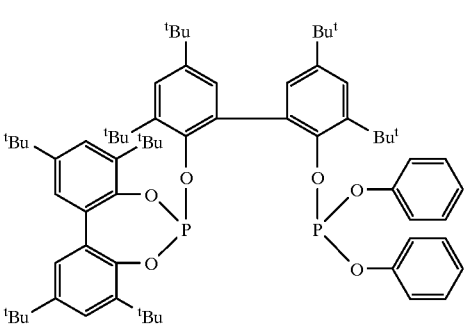
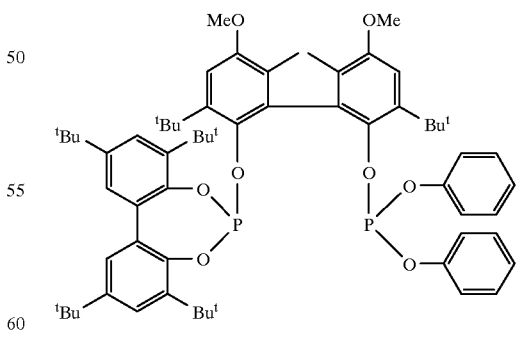

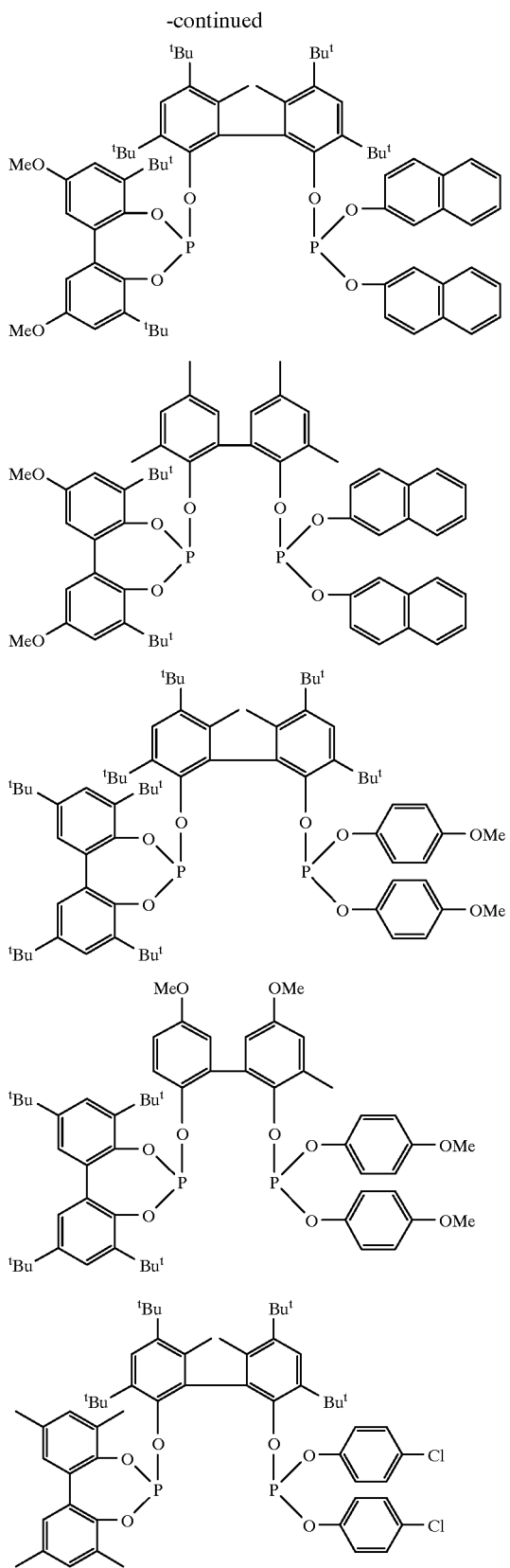
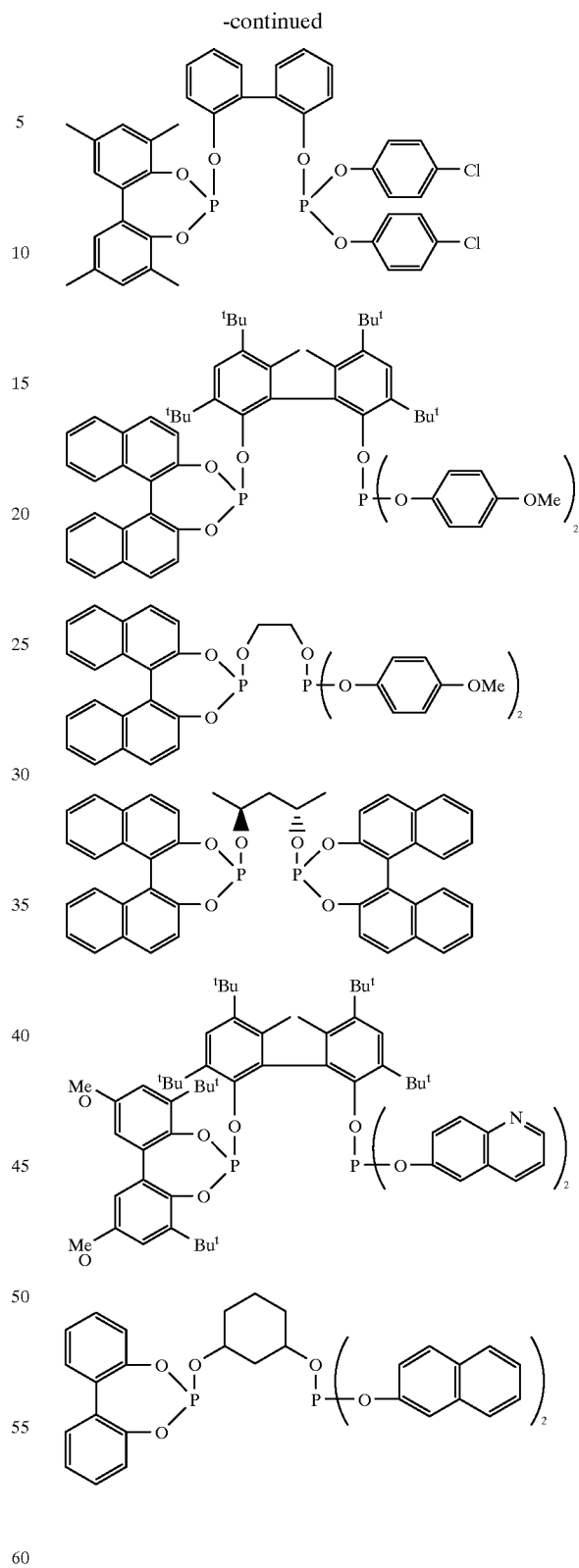

-continued
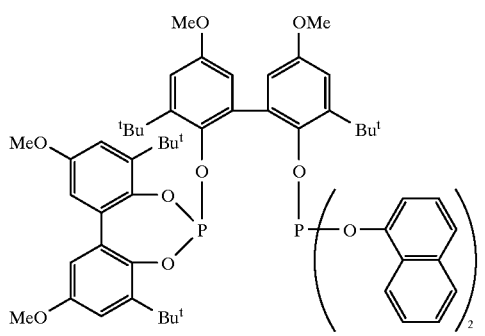
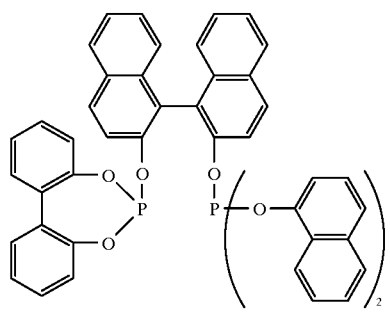
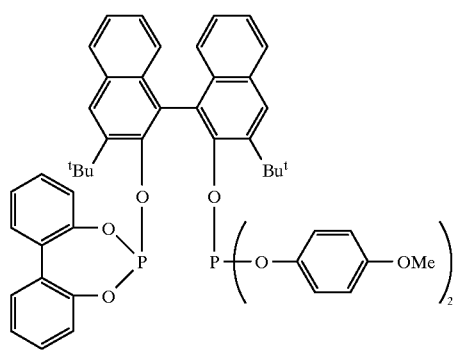
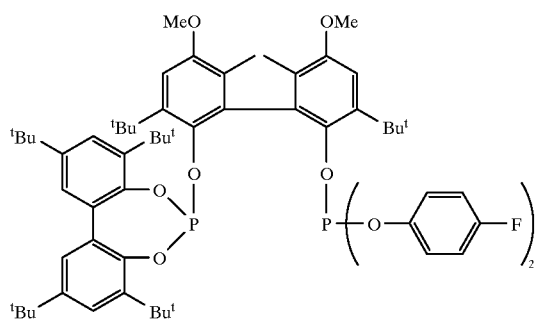
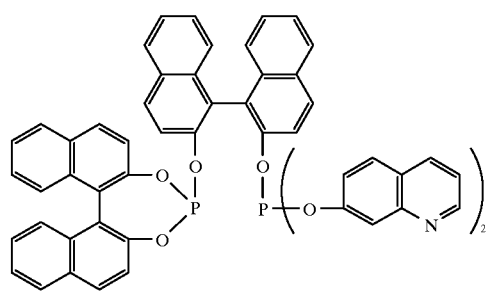
-continued
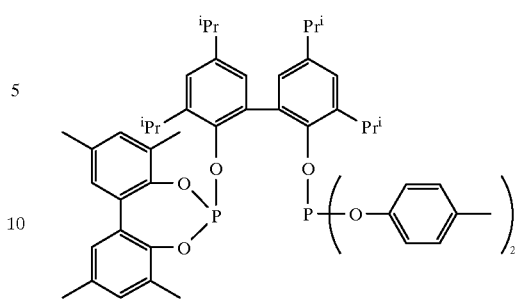
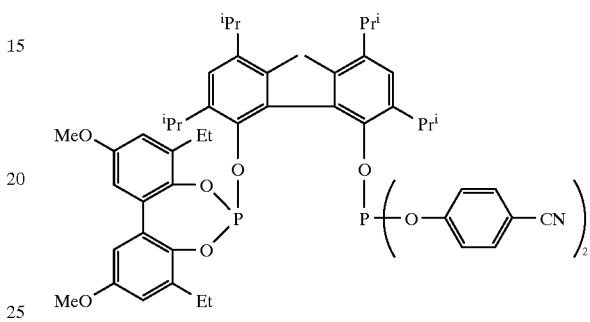
In the formula (II-2), each $Ar^3$ or $Ar^4$ is the same as that defined above for each $Ar^1$ or $Ar^2$. Q* and n* are the same as those defined above for Q and n, respectively.
Examples of the phosphites of the formula (II-2) are shown below:
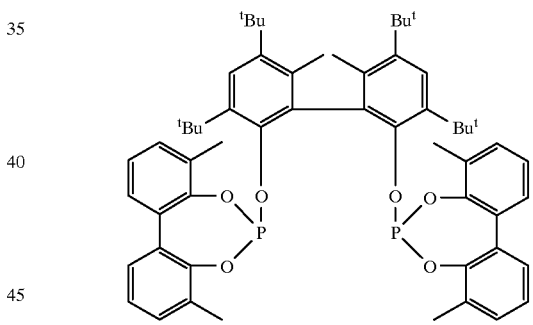
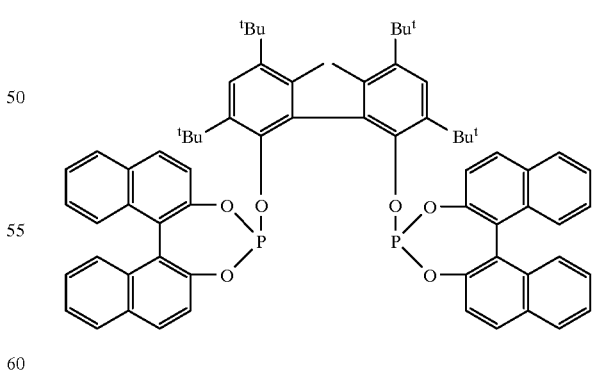

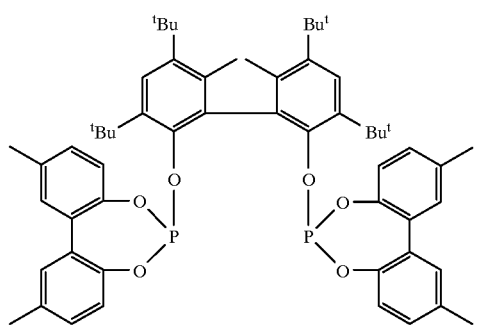
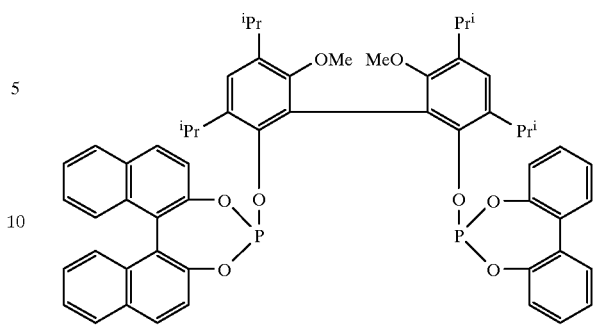
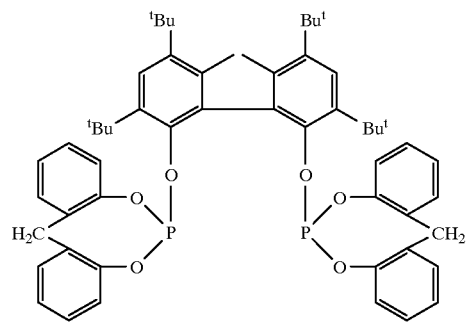
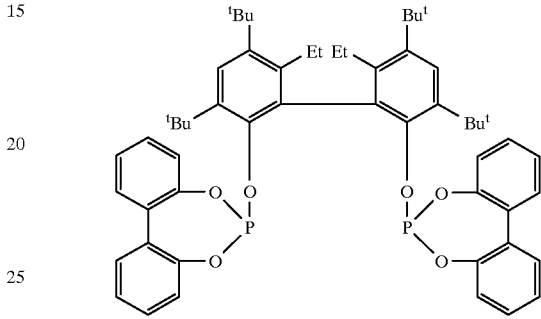
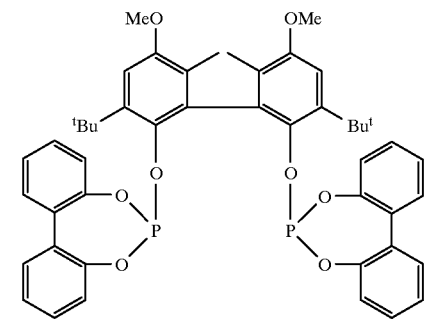
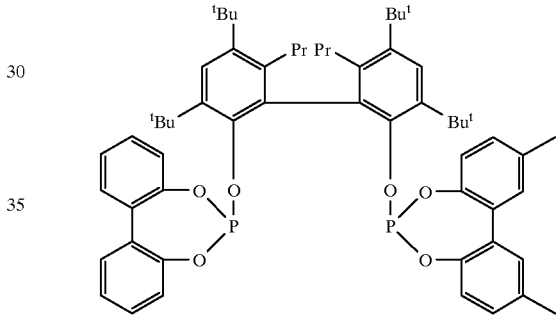
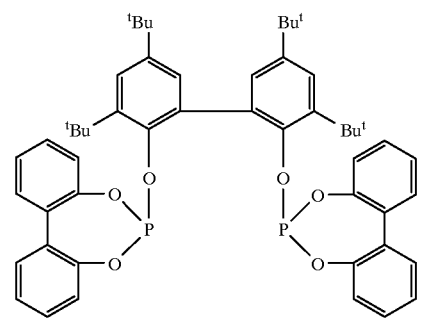
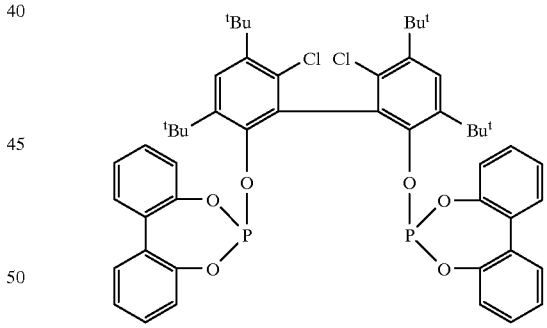
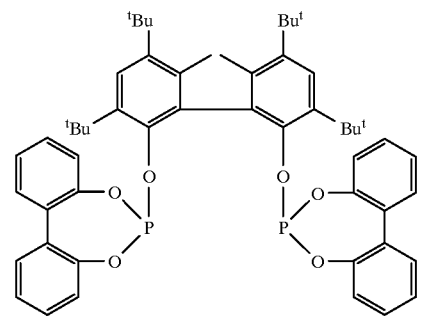
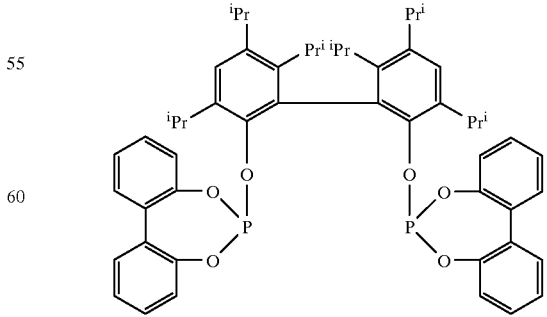

-continued
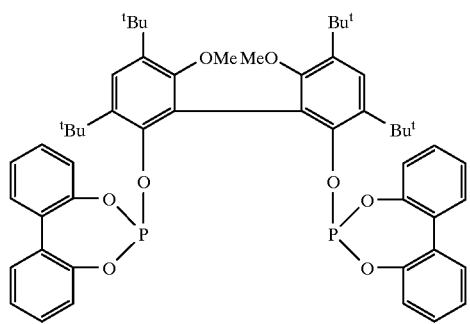
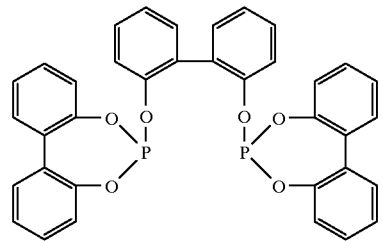
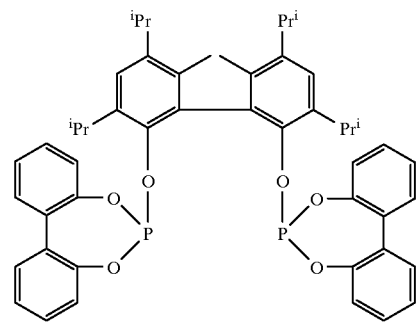
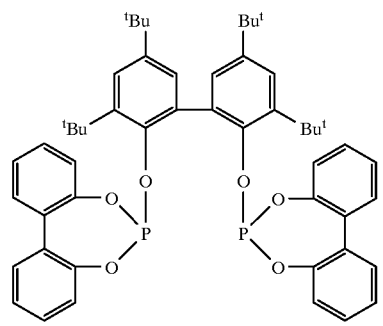
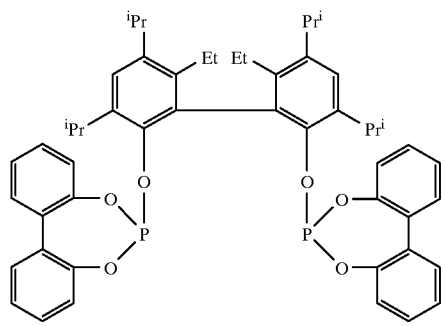
-continued
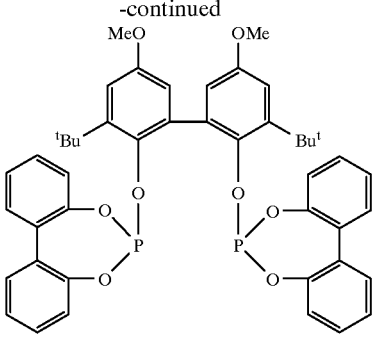
BIPHEPHOS
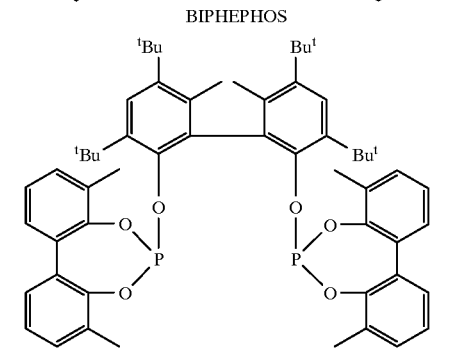
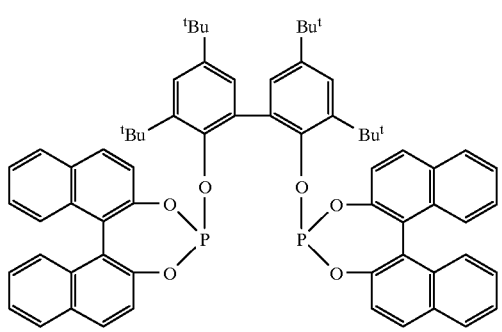
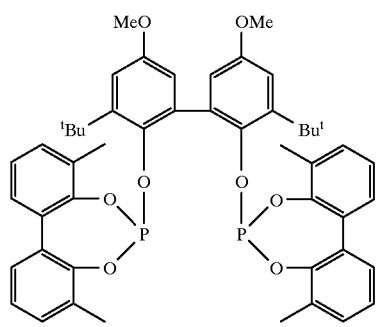
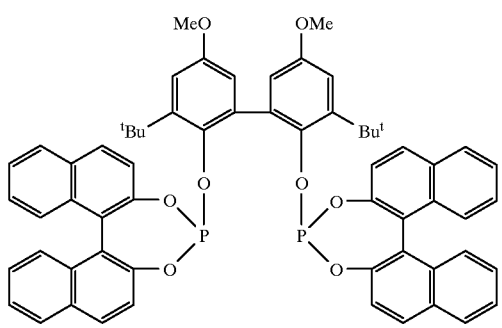

31
-continued
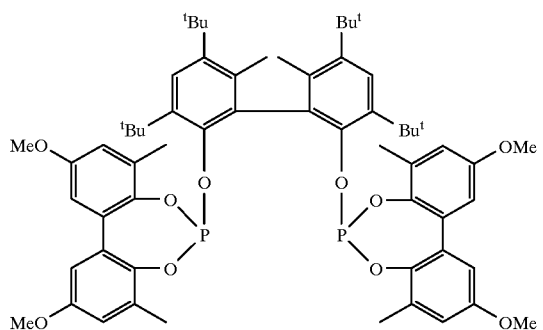
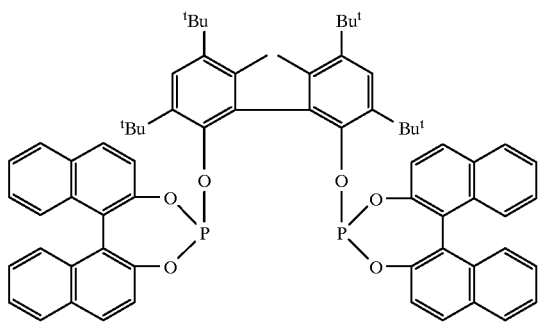
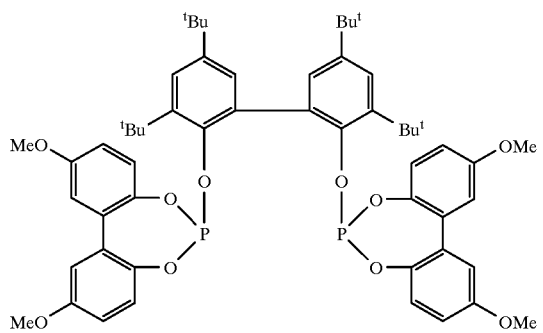
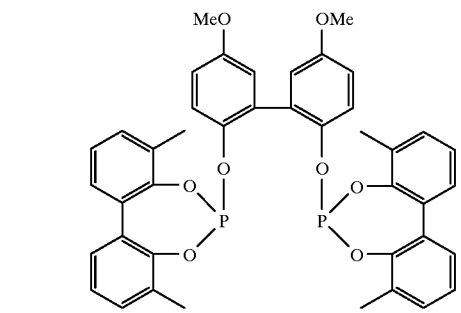
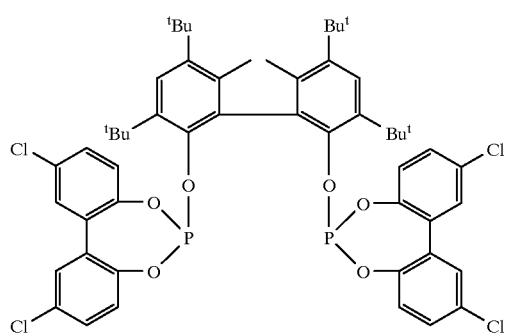
32
-continued
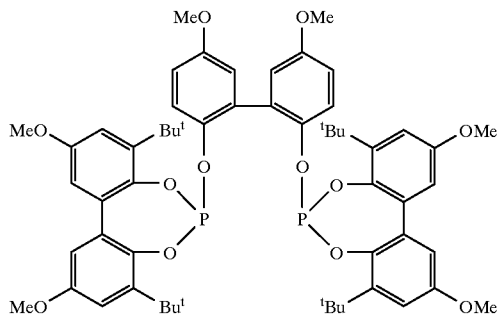
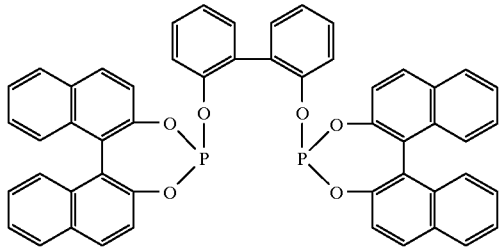
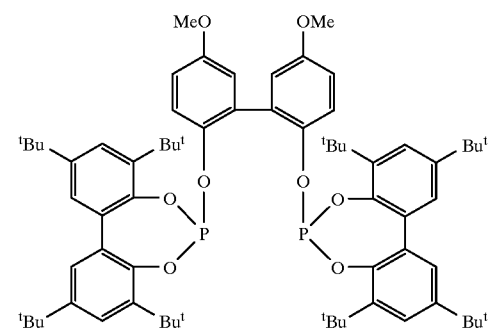
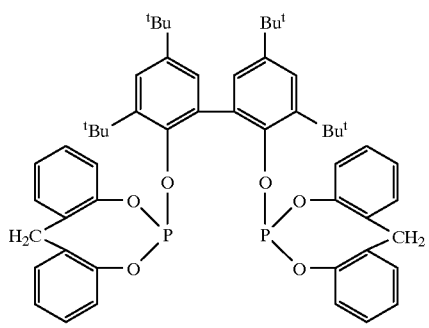
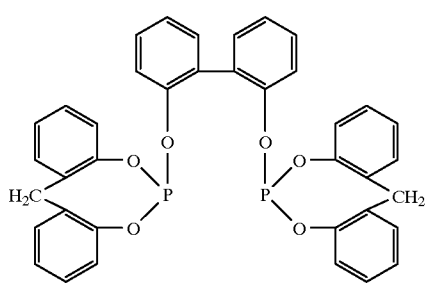

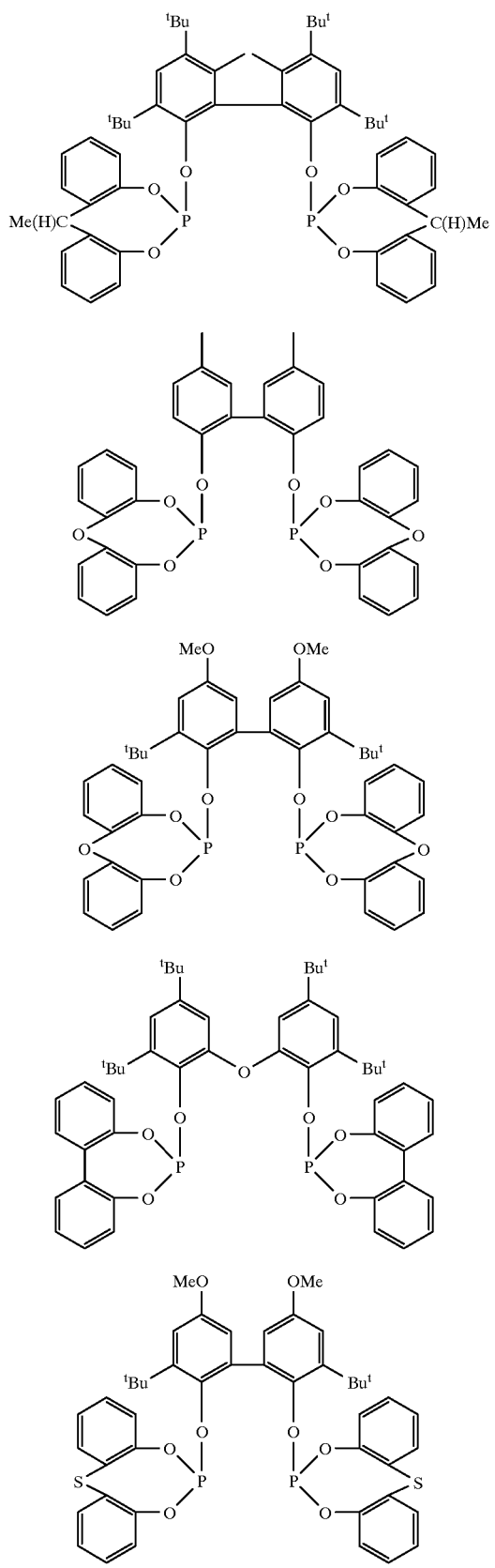
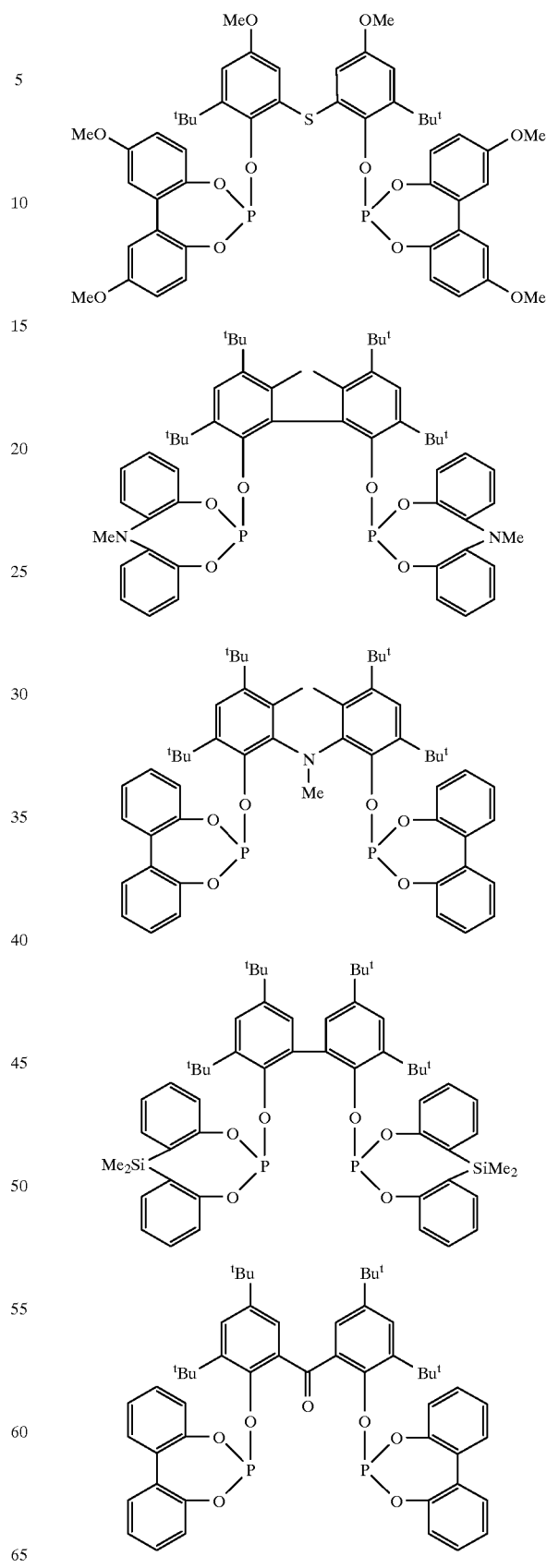

35
-continued
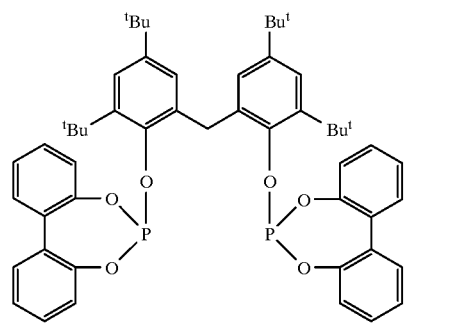
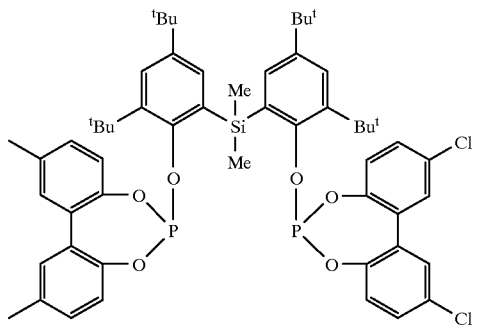
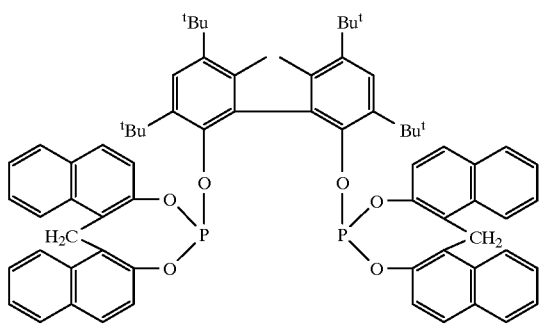
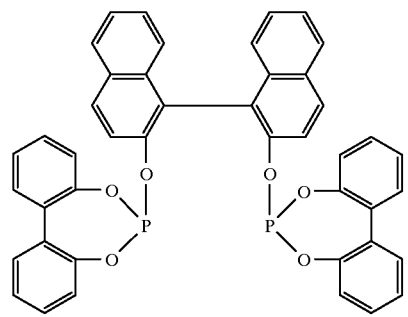
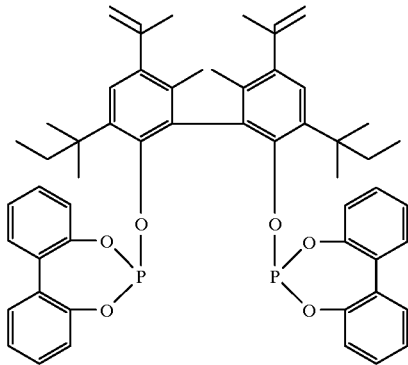
36
-continued
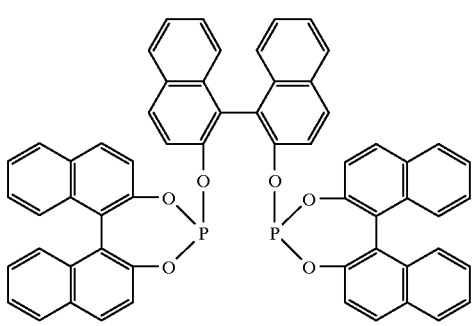
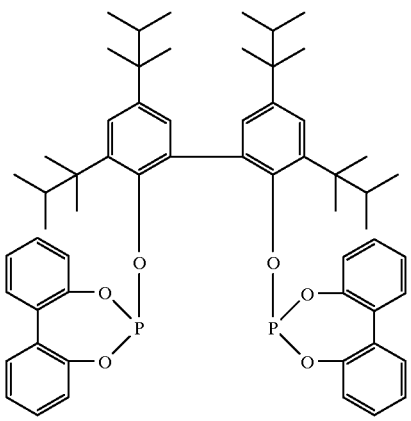
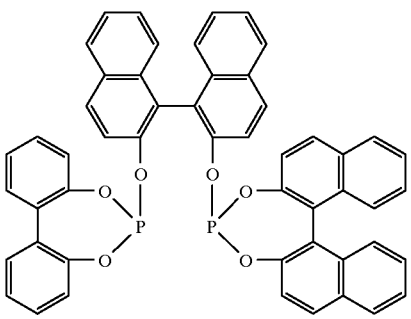
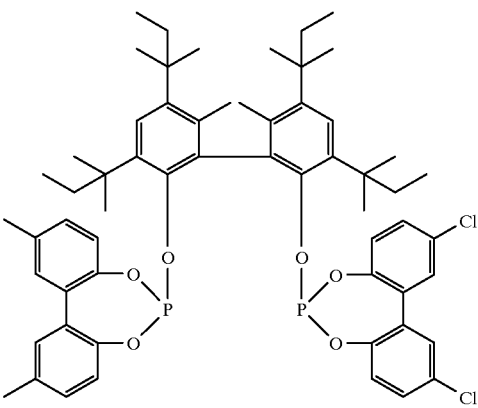

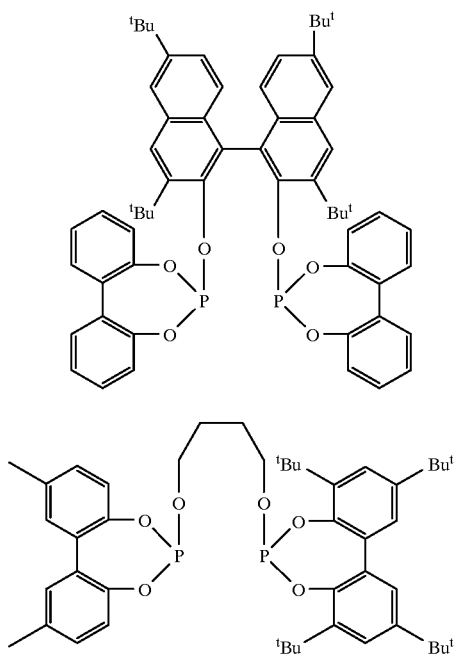
In the formula (III), A and $R^1$ to $R^4$ have been defined above.
Examples of the phosphites of the formula (III) are shown below:
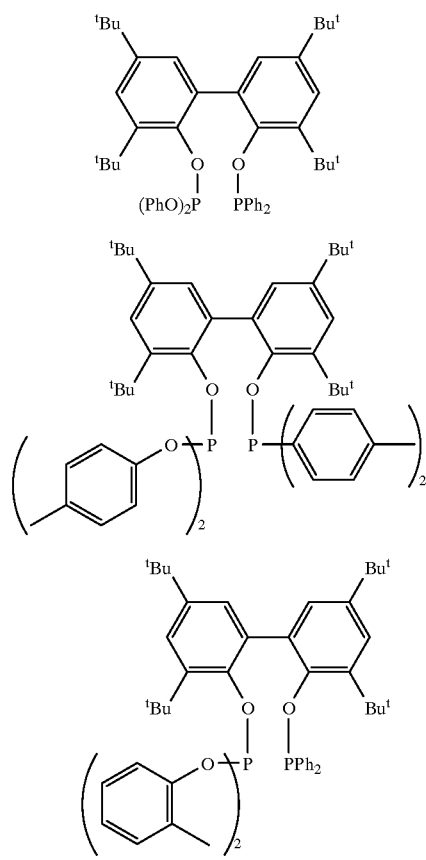
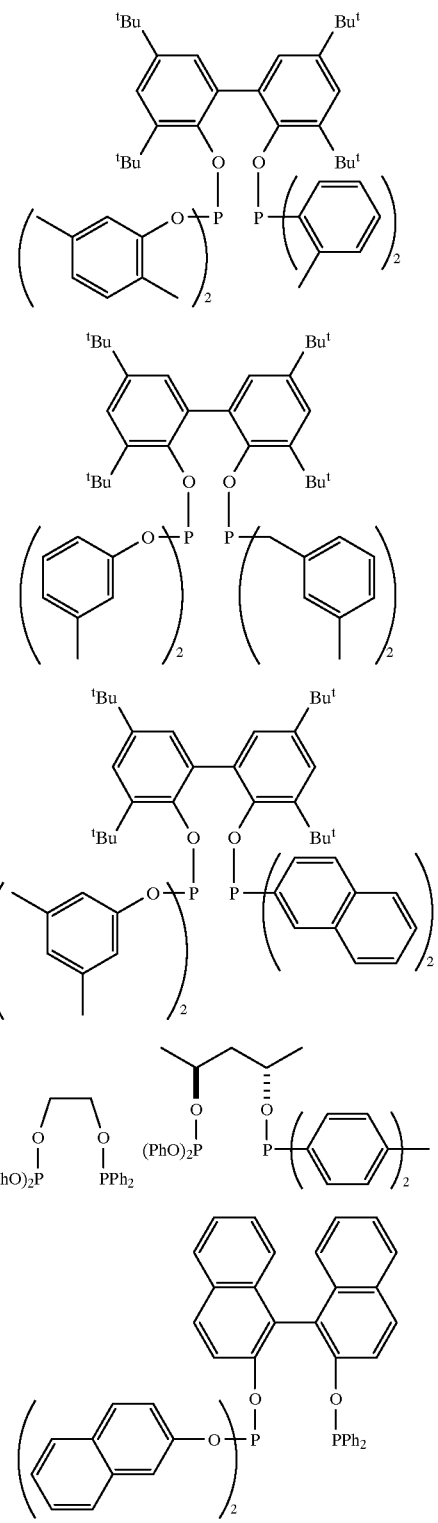

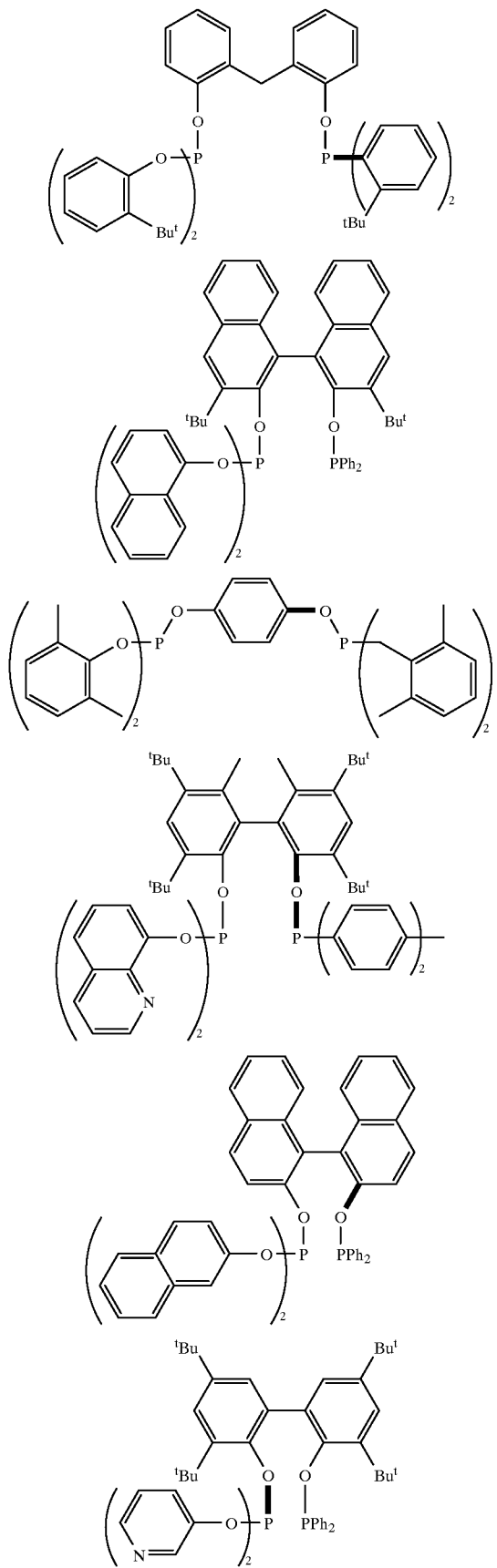
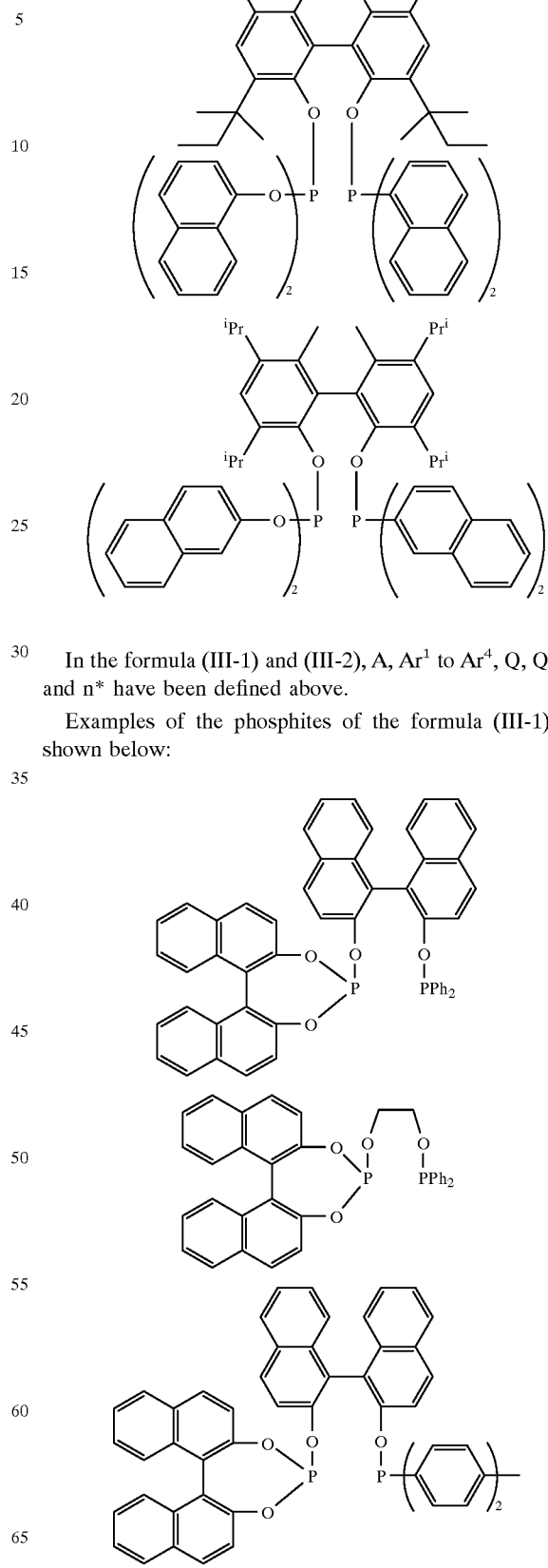
In the formula (III-1) and (III-2), A, $Ar^1$ to $Ar^4$, Q, Q*, n, and n* have been defined above.
Examples of the phosphites of the formula (III-1) are shown below:

-continued
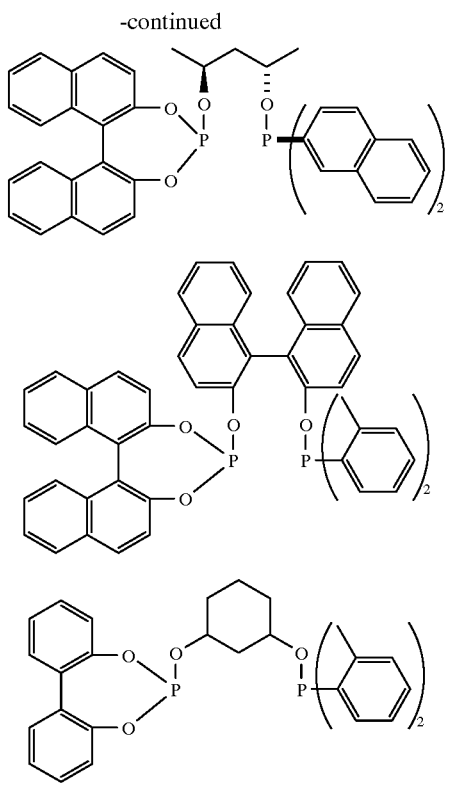
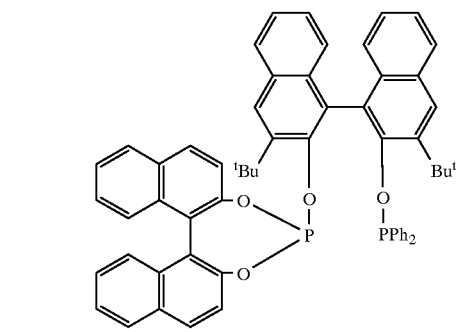
-continued
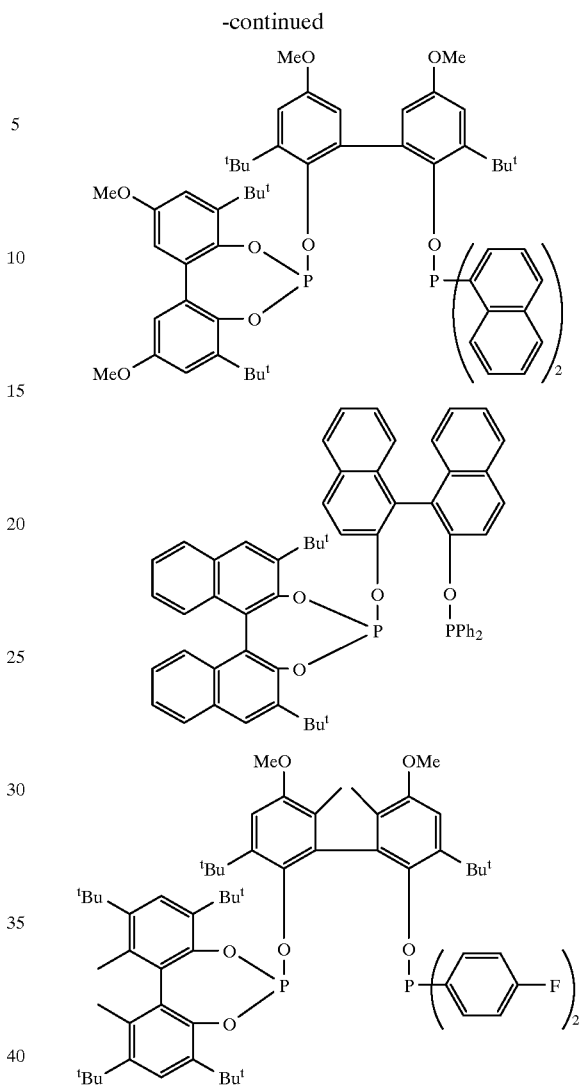
Examples of the phosphites of the formula (III-2) are shown below:
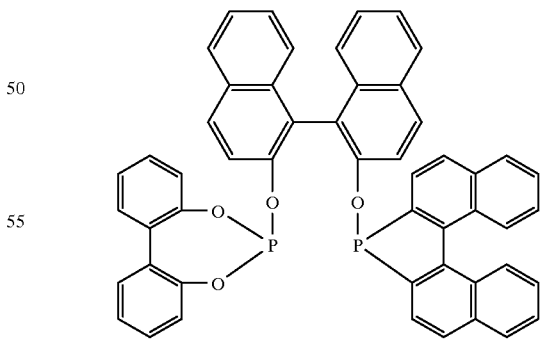
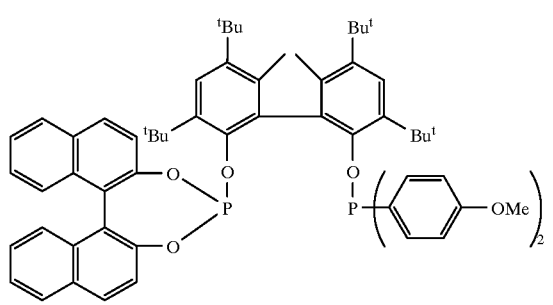

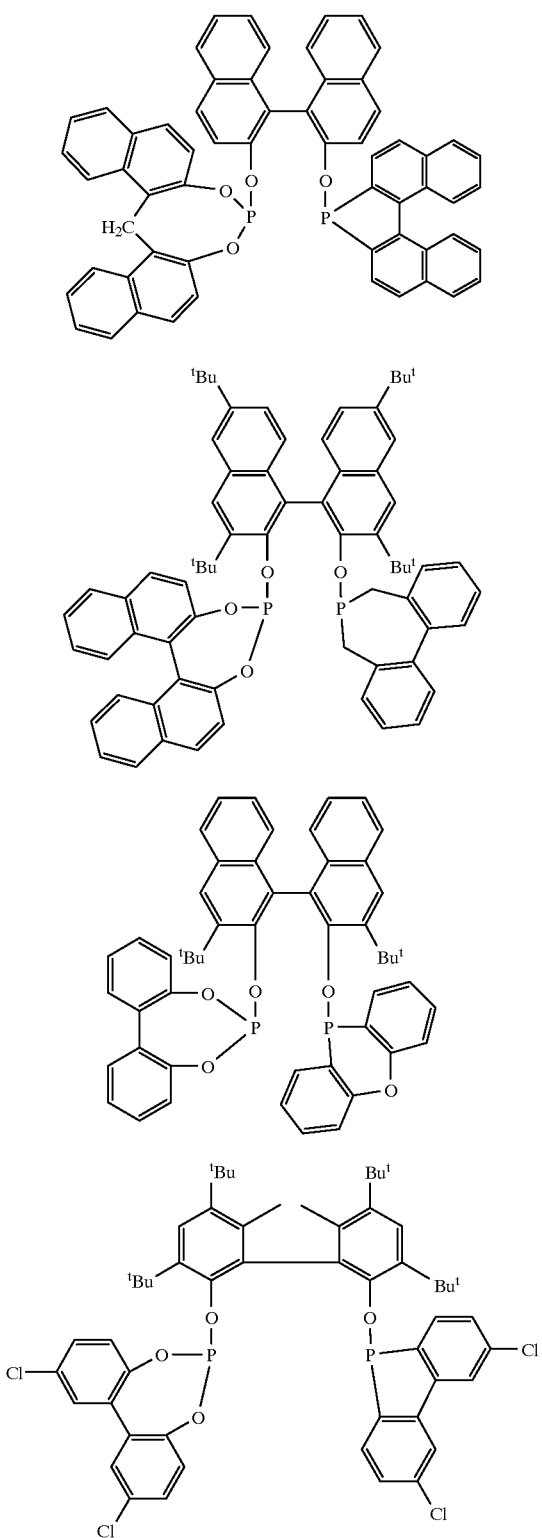
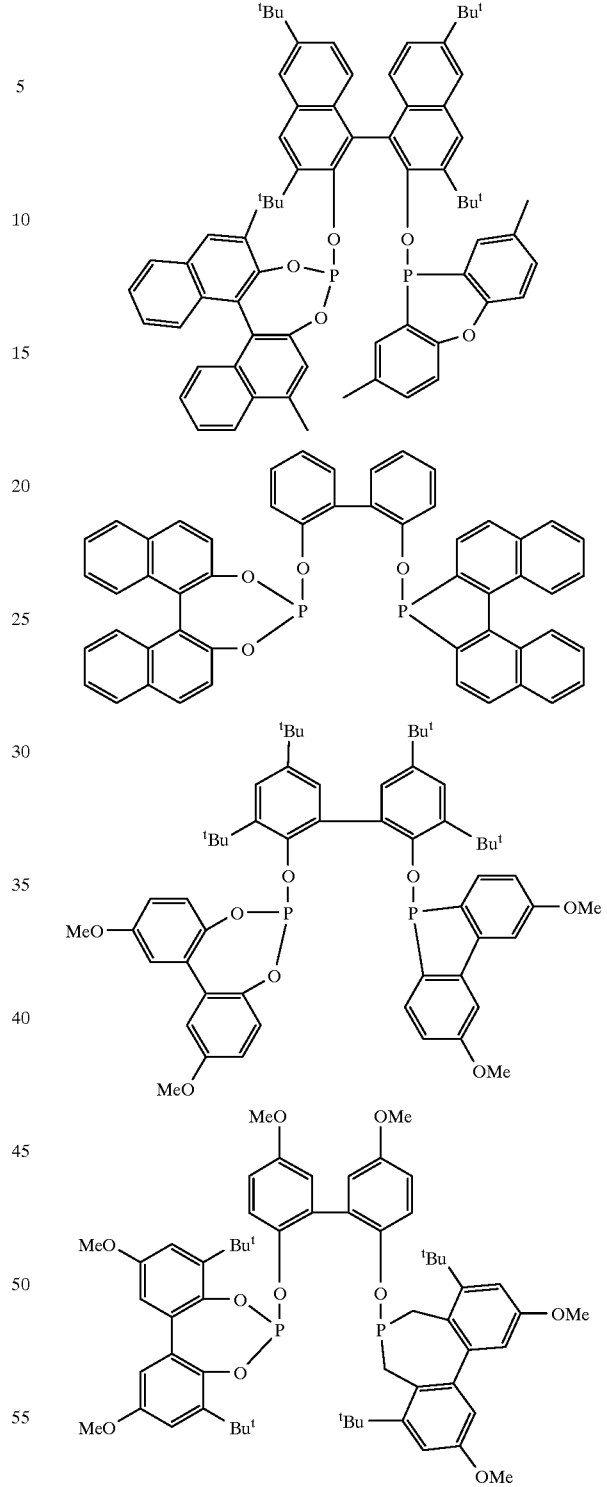
In the formula (IV), A and $R^1$ to $R^4$ have been defined above.
Examples of the phosphites of the formula (IV) are shown below:

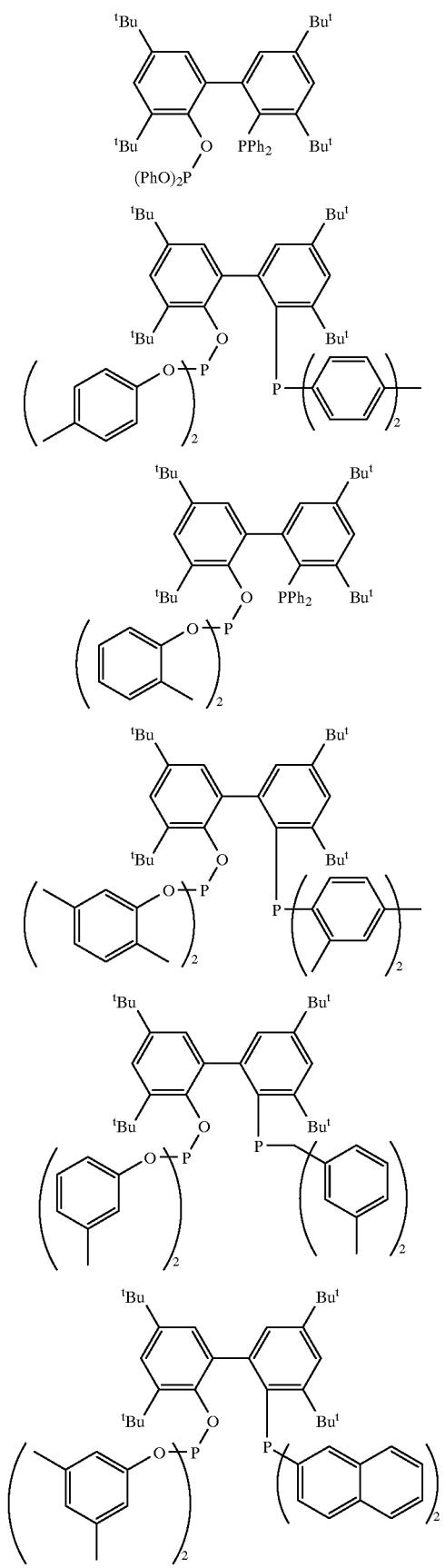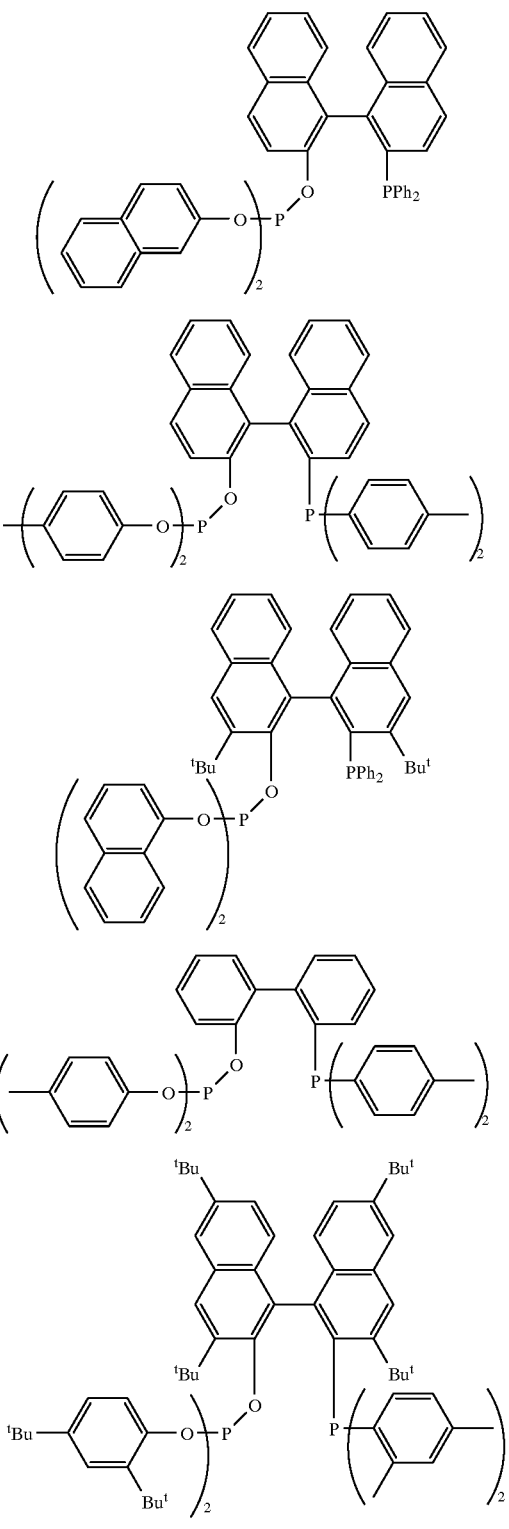
In the formula (IV-1) and (IV-2), A, $Ar^1$ to $Ar^4$, Q, Q*, n, and n* have been defined above.
Examples of the phosphites of the formula (IV-1) are shown below:

47 48
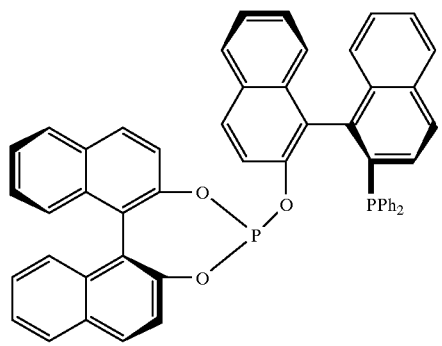
(R,S)-BINAPHOS
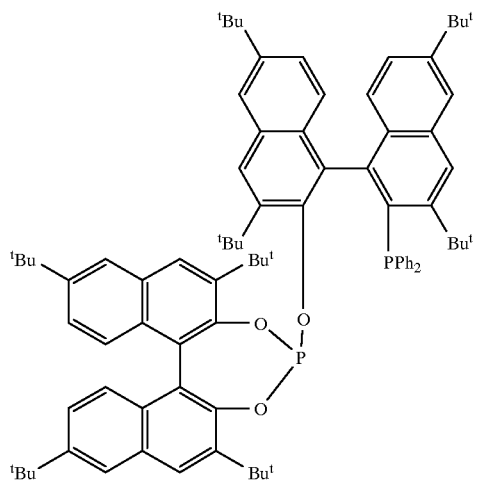
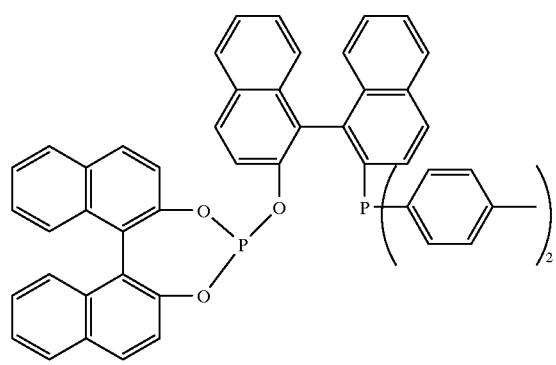
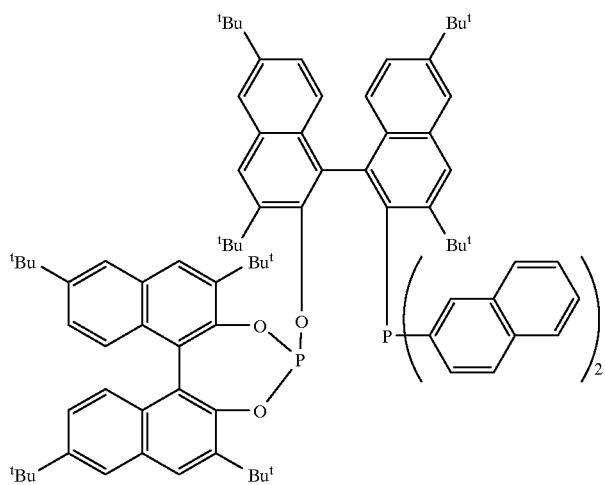
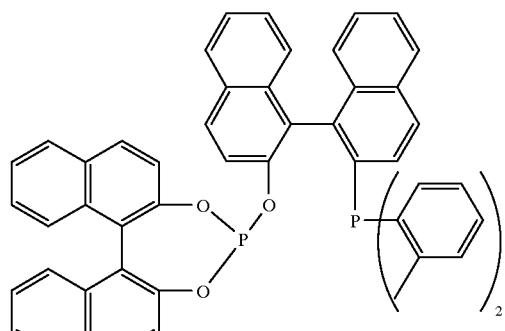
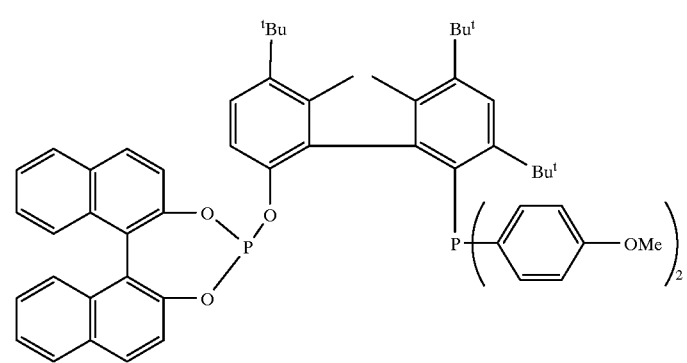

-continued
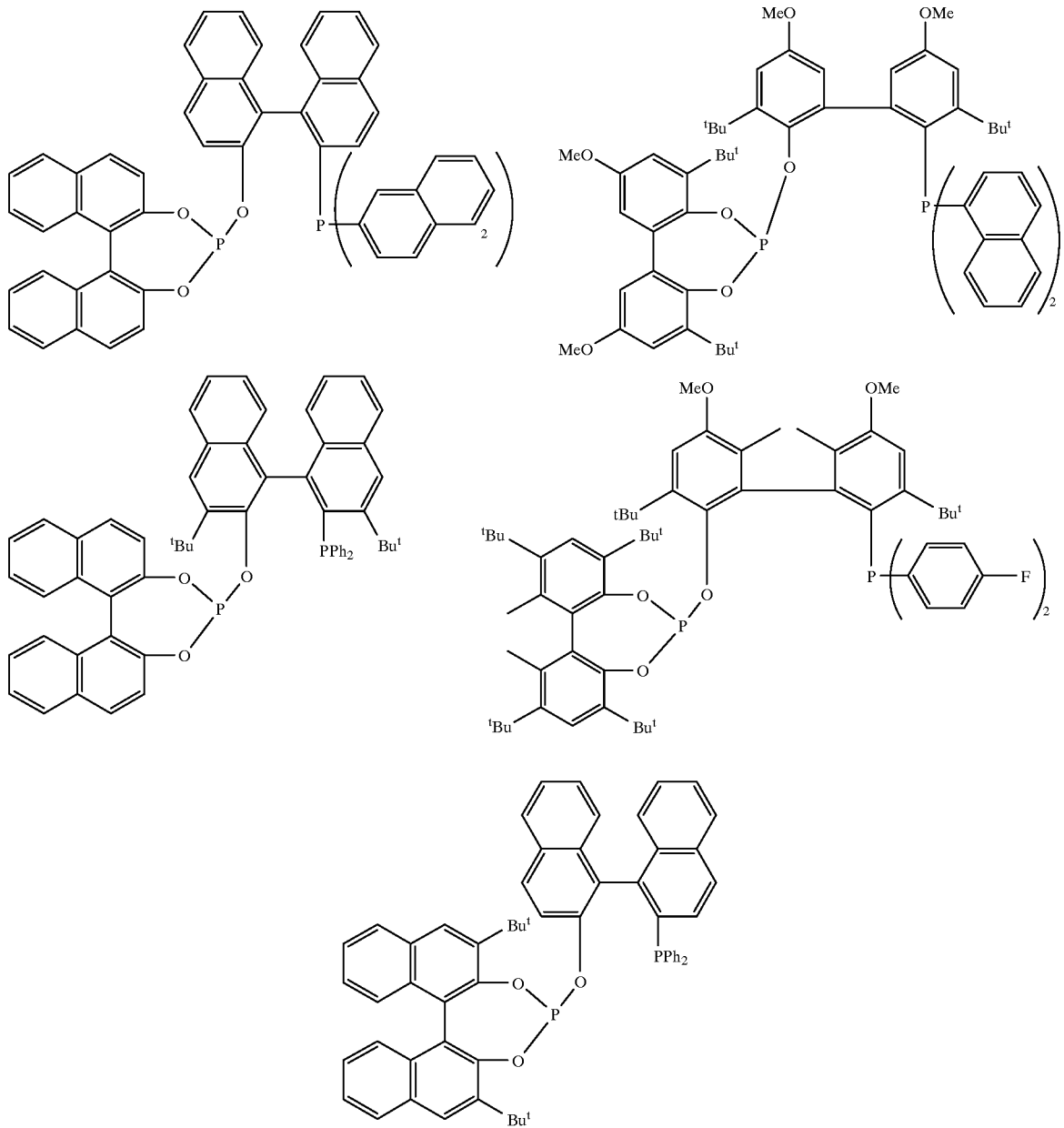
Examples of the phosphites of the formula (IV-2) are shown below:
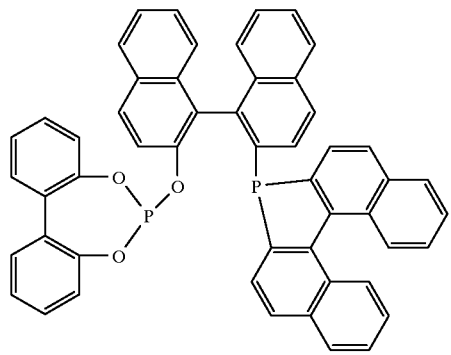

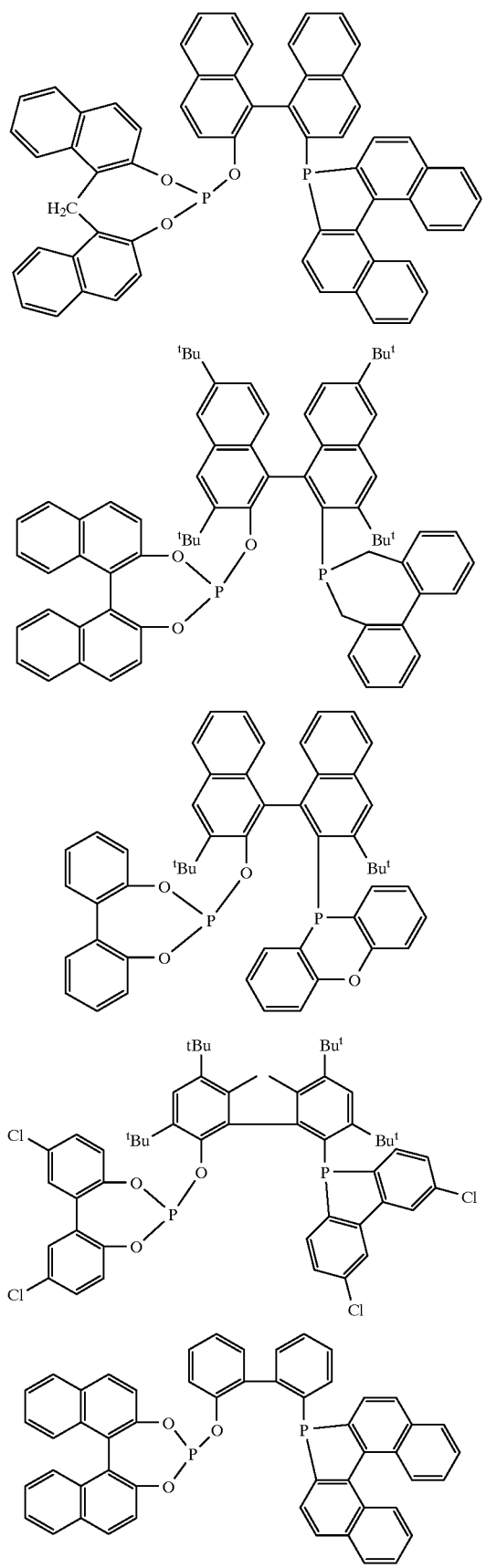
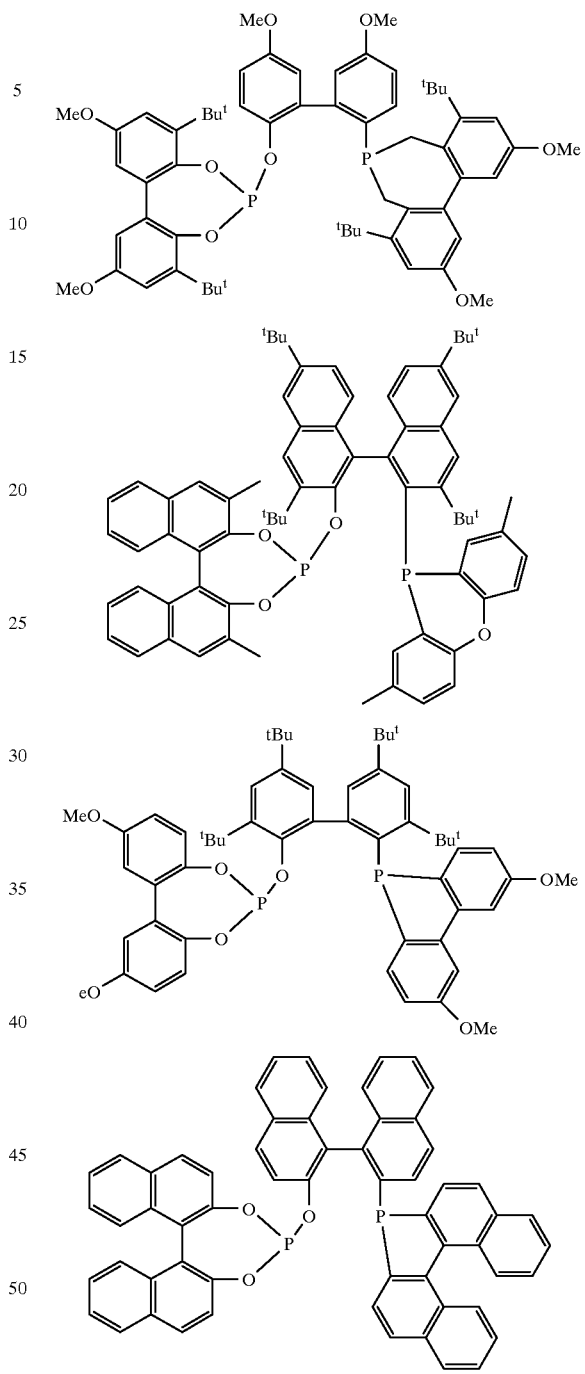

The above phosphite ligands may be used alone or as mixtures thereof.

The amount of the phosphite compound of the present invention is not particularly limited, and it is suitably set to achieve desirable results with respect to the catalytic activity and the product selectivity. It is selected usually in the range from 0.001 to 500 moles, preferably from 0.1 to 100 moles, per mole of Group VIII transition metal.

A wide range of temperature and pressure which maintain the supercritical phase of carbon dioxide can be used. The critical point for scCO$_2$ is known to be 31° C. and 72.9 atm.

Accordingly, the temperatures equal to or higher than 31° C., e.g., 31–150° C., can be used in these processes. Typically, the reactions are run at 35–80° C. The partial pressure of carbon monoxide can be 1~100 atm, preferably 1~50 atm, and partial pressure of hydrogen can be 1~1200 atm, preferably 1~50 atm. The total pressure equal to or higher than 72.9 atm can be used in these processes, preferably in the range of 75 to 200 atm. The ratio of hydrogen to carbon monoxide ($H_2/CO$) is 1/10~10/1, preferably 1/5~5/1.

Typically, the hydroformylation of 1-alkenes such as 1-hexene, 1-octene, 3-phenyl-1-propene, and styrene using $Rh(acac)(CO)_2$ ($6.67 \times 10^{-5}$ M) and a phosphite ligand ($1.33 \times 10^{-4}$ M), typically under 14 atm of $CO/H_2$ (1/1) in $scCO_2$ (85 atm) in a 300 mL stainless steel autoclave equipped with two sapphire windows, proceeds smoothly at 60–65° C. to give a mixture of the corresponding linear and branched aldehydes (equation 1). The ratio of the linear and branched aldehydes is dependent upon the structure of 1-alkene used as well as the phosphite ligand employed. The hydroformylation of vinyl acetate proceeds smoothly under the same reaction conditions to give the branched aldehyde as the predominant product.

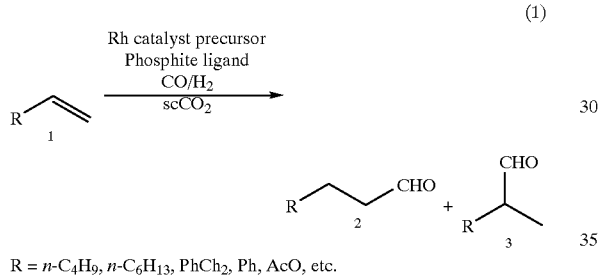

(1)

R = $n$-$C_4H_9$, $n$-$C_6H_{13}$, $PhCh_2$, Ph, AcO, etc.

When a chiral phosphite ligand is used, asymmetric hydroformylation of 1-alkenes (1) takes place to give the corresponding enantiomerically enriched branched aldehydes (3*) together with a small amount of achiral linear aldehydes (2) (equation 2).

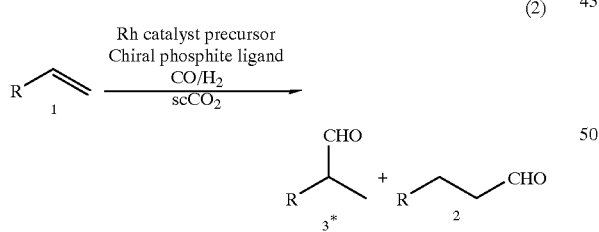

(2)

The hydroformylation of 1-alkynes under the standard conditions mentioned above gives a mixture of saturated aldehydes (2 and 3) (major) and unsaturated aldehydes (5 and 6) (minor) as shown in equation 3. The formation of the corresponding 1-alkene (1) and in some cases isomerized inner alkenes are observed. However, when the reaction is run for a prolonged period of time, only saturated linear aldehyde (2) and branched aldehyde (3) are formed. The result clearly shows that the saturated aldehydes can be formed either through hydroformylation followed by hydrogenation or hydrogenation followed by hydroformylation.

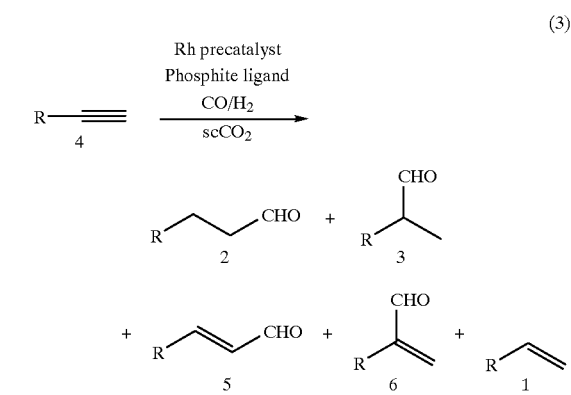

(3)

The hydroformylation of 1,3-dienes requires higher temperatures to proceed smoothly. For example, the hydroformylation of isoprene (7) catalyzed by a rhodium-phosphite complex using 14 atm of hydrogen (initial pressure at room temperature), 7 atm of carbon monoxide (initial pressure at room temperature) at 120° C. and 100 atm (total pressure) in supercritical carbon dioxide gives 1,4-conjugate hydroformylation product (8) as the predominant product together with a small amount of 1,2-hydroformylation product (9) with high regioselectivity (equation 4).

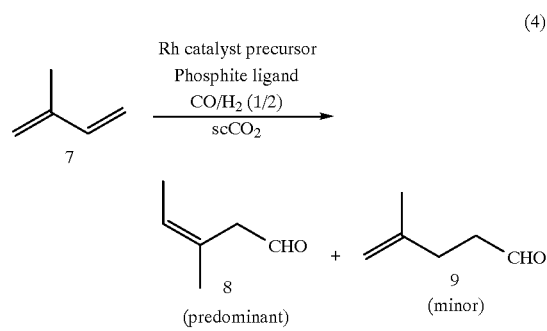

(4)

The cyclohydrocarbonylation of (S)-N-t-Boc-allylglycinate (10) under the standard conditions mentioned above proceeded cleanly to yield (S)-2-methoxycarbonyl-5,6-didehydropipecolate (11) as the sole product in quantitative yield (equation 5). No racemization takes place during the process. A similar result was observed when the reaction was carried out in THF, toluene, ethyl acetate, chloroform or hexane. Thus. it is apparent that $scCO_2$ can nicely replace these traditional organic solvents for this reaction. The 5,6-didehydropipecolate (11) thus obtained serves as a useful intermediate for pharmaceuticals and agrochemicals.

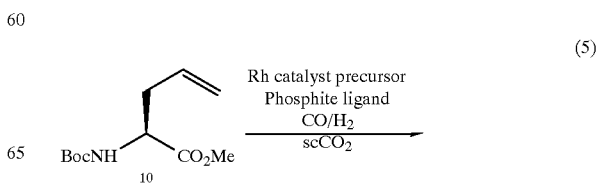

(5)

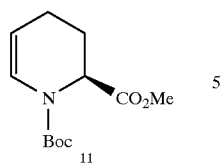

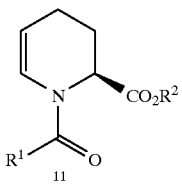

The most likely mechanism for the intramolecular cyclohydrocarbonylation is illustrated in Scheme 1. The first step of this process is an extremely regioselective hydroformylation of N-t-Boc-allylglycinate (10), giving the linear aldehyde (12) followed by cyclization to form 13. The hemiamidal (13) eliminates a hydroxyl group, generating an reactive acyliminium ion intermediate 14, which gives 5,6-dehydropiperidine (11) via double bond migration.

The reaction of 4-(t-Boc-amino)-1,6-heptadiene (15) under the standard conditions gave 1-t-Boc-2-(3-formylpropyl)-5,6-didehydropiperidine (16) exclusively in quantitative yield (eq. 6). Accordingly, $scCO_2$ proves to be an excellent reaction medium for this reaction. As a protecting group of 4-amino moiety, other common protecting groups such as p-toluenesulfonyl, benzyloxycarbonyl (Cbz), methoxylcarbonyl, etc., can be used. The compound 16 serves as a useful intermediate for a variety of nitrogen heterocycles and alkaloids as pharmaceuticals and argochemicals.

Scheme 1

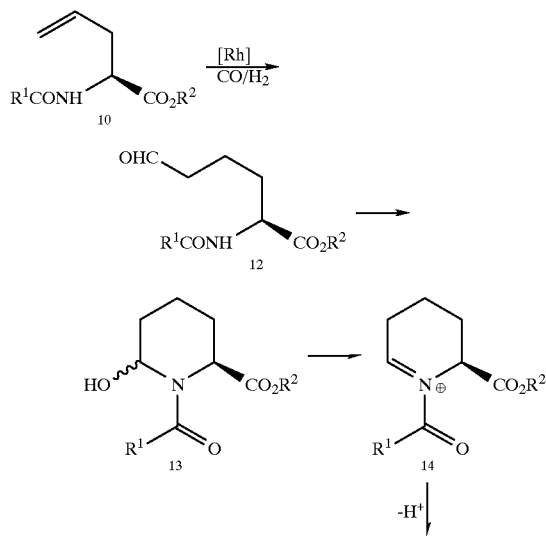

(6)

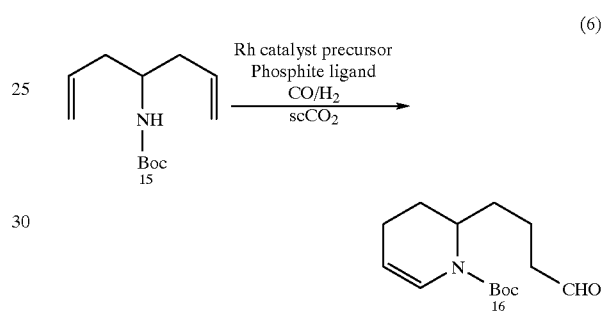

The most likely mechanism for the formation of 16 is shown in Scheme 2. The first step is the linear-selective hydroformylation of one of the two double bonds giving 17 which is followed by cyclization to give alkenyl-hemiamidal 18. The hydroformylation of the remaining double bond takes place to afford hemiamidal-aldehyde 19. Then, 19 undergoes dehydration via an iminium ion intermediate 20 to yield 16.

Scheme 2

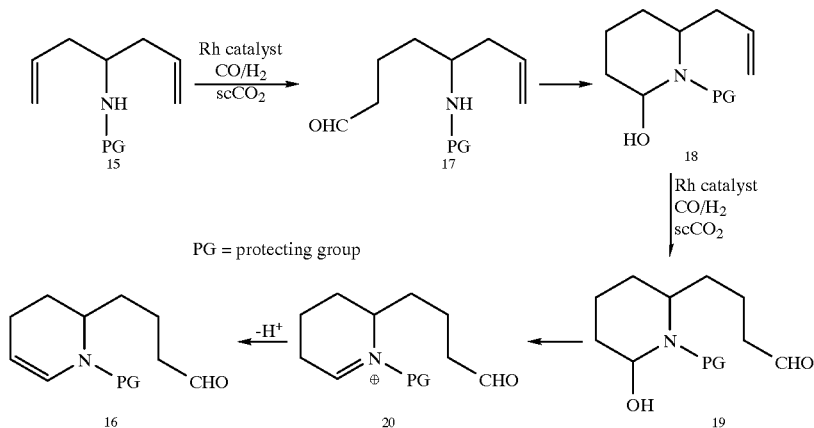

PG = protecting group

In a similar manner, the reaction of 1,6-heptadien-4-ol (21) in scCO$_2$ under the standard conditions afforded lactol-aldehyde (22) in quantitative yield (equation 7). The lactol-aldehyde (22) serves as a useful intermediate for pharmaceuticals and agrochemicals.

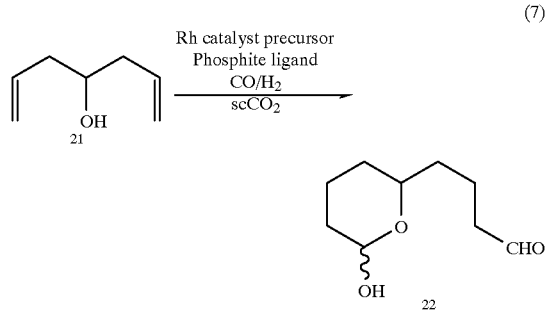

(7)

The following non-limiting examples are illustrative of the present invention. It should be noted that various chances would be made in the above examples and processes therein without departing from the scope of the present invention. For this reason, it is intended that the illustrative embodiments of the present application should be interpreted as being illustrative and not limiting in any sense.

EXAMPLES 1–17

The names of some phosphite ligands in the EXAMPLES are abbreviated: BIPHEPHOS stands for O,O'-[[3,3'-bis(1,1-dimethylethyl)-5,5'-dimethoxy[1,1'-biphenyl]-2,2'-diyl]bis(oxy)]bisdibenzo[d,f][1,3,2]dioxaphosphepin [E. Billig, A. G. Abatjoglou, and D. R. Bryant, U.S. Pat. No. 4,769,498 (1988)]; MCP-1 stands for 3,3',5,5'-tetra-(1,1-dimethylethyl)-2,2'-bis[bis[(2-naphthyloxy)phosphino]oxy]biphenyl [H. Urata, H. Itagaki, E. Takahashi, Y. Wada, Y. Tanaka, and Y. Ogino, Japan Patent Application, Heisei 9-107327 (1997)]; MCP-2 stands for 3,3',5,5'-tetra-(1,1-dimethylethyl)-6,6'-dimethyl- 2,2'-bis[bis[(1-naphthyloxy)phosphino]oxy]biphenyl [H. Urata, H. Itagaki. E. Takahashi, Y. Wada, Y. Tanaka, and Y. Ogino, Japan Patent Application, Heisei 9-107327 (1997)]; BINAPHOS stands for 4-[[2'-(diphenylphoshino)[1,1'-binaphthalen]-2-yl]oxy]dinaphtho[2,1-d:1',2'-f][1,3,2]dioxaphosphepin [N. Sakai, S. Mano, K. Nozaki, H. Takaya, J. Am. Chem. Soc. 115, 7033–7034 (1993)].

General procedure for hydroformylation of 1-alkenes in sCCO$_2$

To a 300 mL stainless steel autoclave equipped with two sapphire windows containing Rh(acac)(CO)$_2$ (5.2 mg, 2×10$^{-2}$ mmol) and a phosphite ligand (4×10$^{-2}$ mmol) were added 2.0 mmol of alkene and 2.0 mmol of n-octane (internal standard). The air was replaced by CO through pressurization (2–3 atm) and release for 2–3 times, and CO (7 atm) was introduced followed by H$_2$ (7 atm). The reaction vessel was cooled to −60° C. and CO$_2$ (85 atm) was introduced. The mixture was allowed to stir at 60–65° C. and 100 atm overnight. The autoclave was cooled to 0° C. and all the gasses were carefully released. The conversion and yield of the reaction was estimated by GC analysis using an authentic sample of the aldehyde and n-octane as the internal standard. Products of each reaction are also identifiled by $^1$H NMR analysis.

TABLE 1

Hydroformylation of 1-alkenes in scCO$_2$.

| Example | Substrate | Phosphite ligand | Product(s) | Conv. (%) | linear/branch ratio |
|---|---|---|---|---|---|
| 1 | 1-hexene | BIPHEPHOS | 1-heptanal<br>2-methylhexanal<br>3-phenyl-1-butanal | 100 | 3/1 |
| 2 | 3-phenyl-1-propene | BIPHEPHOS | 3-phenyl-2-methyl-1-propanal | 100 | 28/1 |
| 3 | 1-octene | BIPHEPHOS | 1-nonanal<br>2-methylheptanal | 100 | 170/1[a] |
| 4 | 1-octene | MCP-1 | 1-nonanal<br>2-methylheptanal | 100 | 90/1[a] |
| 5 | 1-octene | MCP-2 | 1-nonanal<br>2-methylheptanal | 100 | 42/1 |
| 6 | 1-octene | (BuO)$_3$P | 1-nonanal<br>2-methylheptanal | 100 | 2.3/1 |
| 7 | styrene | BIPHEPHOS | 3-phenylpropanal<br>2-phenylpropanal | 100 | 1/7.3 |
| 8 | styrene | MCP- | 3-phenylpropanal<br>2-phenylpropanal | 99 | 1/3.2[b] |
| 9 | styrene | MCP-2 | 3-phenylpropanal<br>2-phenylpropanal | 78 | 2/1 |
| 10 | styrene | (BuO)$_3$P | 3-phenylpropanal<br>2-phenylpropanal | 25 | 1/12.5 |
| 11 | styrene | BINAPHOS | 3-phenylpropanal<br>2-phenylpropanal | 91 | 1/12.5[b,c] |
| 12 | vinyl acetate | BIPHEPHOS | 3-acetoxylpropanal<br>2-acetoxypropanal | 100 | 1/18 |
| 13 | vinyl acetate | MCP-1 | 3-acetoxylpropanal<br>2-acetoxypropanal | 100 | 1/13 |
| 14 | cyclohexene | MCP-1 | formylcyclohexane | 90 | — |

TABLE 1-continued

Hydroformylation of 1-alkenes in scCO$_2$.

| Example | Substrate | Phosphite ligand | Product(s) | Conv. (%) | linear/branch ratio |
|---|---|---|---|---|---|
| 15 | 4-vinylcyclohex-1-ene | BIPHEPHOS | 3-(cyclohex-3-enyl)-propanal 2-(cyclohex-3-enyl)-propanal | 80 | 3.3/1 |
| 16 | 4-vinylcyclohex-1-ene | MCP-1 | 3-(cyclohex-3-enyl)-propanal 2-(cyclohex-3-enyl)-propanal | 95 | 5.8/1 |
| 17 | 4-vinylcyclohex-1-ene | MCP-2 | 3-(cyclohex-3-enyl)-propanal 2-(cyclohex-3-enyl)-propanal | 98 | 13.8/1 |

[a] Reaction was run under 73 atm of scCO$_2$.
[b] Reaction was run 21 atm of H$_2$/CO (2/1) and 78 atm of scCO$_2$.
[c] Rh(acac)(CO)$_2$ (4 × 10$^{-2}$ mmol) and phosphite ligand (8 × 10$^{-2}$ mmol) were employed.

EXAMPLE 18

To a 300 mL stainless steel autoclave equipped with two sapphire windows containing Rh(acac)(CO)$_2$ (10.4 mg, 4×10$^{-2}$ mmol) and (R,S)-BINAPHOS (60 mg, 8×10$^{-2}$ mmol) were added styrene (2.08 g, 2.0 mmol) and n-undecane (156 mg, 1.0 mmol) (the internal standard for GC analysis). The air was replaced by CO through pressurization (2–3 atm) and release for 2–3 times, and CO (7 atm) was introduced followed by H$_2$ (14 atm). The reaction vessel was cooled to −60° C. and CO$_2$ (78 atm) was introduced. The mixture was allowed to stir at 65° C. and 100 atm overnight. The autoclave was cooled to 0° C. and all the gasses were carefully released. The GC analysis showed that the conversion of the reaction was 91% and the ratio of 3-phenylpropanal to (R)-2-phenylpropanal was 1:12.5. The enantiomeric purity of 2-phenylpropanal thus formed was determined to be 85% enantiomeric excess by converting it to (R)-2-phenylpropanol followed by esterification with (S)-methoxy(trifluoromethyl)phenylacetyl chloride in the presence of triethylamine in CH$_2$Cl$_2$, and subjecting the resulting chiral ester to the $^1$H NMR analysis.

EXAMPLE 19
Hydroformylation of phenylacetylene in scCO$_2$

To a 300 mL stainless steel autoclave equipped with two sapphire windows containing Rh(acac)(CO)$_2$ (10.4 mg, 4×10$^{-2}$ mmol) and MCP-1 (83.5 mg, 8×10$^{-2}$ mmol) was added phenylacetylene (409 mg, 4.0 mmol). The air was replaced by CO through pressurization (2–3 atm) and release for 2–3 times, and CO (7 atm) was introduced followed by H$_2$ (7 atm). The reaction vessel was cooled to −60° C. and CO$_2$ (85 atm) was introduced. The mixture was allowed to stir at 67° C. and 100 atm for 38 h. The autoclave was cooled to 0° C. and all the gasses were carefully released. The GC as well as $^1$H NMR analyses of the reaction mixture indicated the complete conversion, and the formation of 3-phenylpropanal (43%) and 2-phenylpropanal (57%). The structures of products were identified both by comparison with authentic samples based on GC analysis and by $^1$H NMR analyses.

When MCP-2 (85.7 mg, 8×10$^{-2}$ mmol) was employed as the phosphite ligand and the hydroformylation of phenylacetylene was carried out under the same conditions as described above, 3-phenylpropanal (62%) was formed as the major product together with 2-phenylpropanal (18%) and styrene (20%) at 80% conversion.

EXAMPLE 20

To a 300 mL stainless steel autoclave equipped with two sapphire windows containing Rh(acac)(CO)$_2$ (10.4 mg, 4×10$^{-2}$ mmol) and phosphite ligand MCP-1 (8×10$^{-2}$ mmol) was added phenylacetylene (204 mg, 2.0 mmol) and n-undecane (156 mg, 1.0 mmol) (the internal standard for GC analysis). The air was replaced by CO through pressurization (2–3 atm) and release for 2–3 times, and CO (7 atm) was introduced followed by H$_2$ (14 atm). The reaction vessel was cooled to −60° C. and CO$_2$ (78 atm) was introduced. The mixture was allowed to stir at 60° C. and 100 atm for 20 h. The autoclave was cooled to 0° C. and all the gasses were carefully released. The conversion of the reaction was estimated by $^1$H NMR analysis and the products ratio and yields were determined by GLC analysis using an authentic sample of each aldehyde. Products were also identified by $^1$H NMR analyses. Under these conditions, a considerable amount of styrene formed through hydrogenation of phenylacetylene remained unreacted (20%) at 80% conversion. A mixture of saturated and unsaturated aldehydes was formed in 60% yield, which consisted of 3-phenylpropanal (46%). 2-phenylpropanal (48%), 3-phenylpropenal (0.4%), and 2-phenylpropenal (5.6%).

EXAMPLE 21
Hydroformylation of isoprene in scCO$_2$

To a 125 mL stainless steel autoclave equipped with two sapphire windows containing Rh(acac)(CO)$_2$ (20.8 mg, 0.08 mmol) and MCP-1 (0.12 mmol) were added 10.0 mmol of isoprene (1.0 mL, 10.0 mmol) and n-heptane (0.73 mL, 5.0 mmol) (the internal standard for GC analysis). The air was replaced by CO through pressurization (2–3 atm) and release for 2–3 times, and CO (7 atm) was introduced followed by H$_2$ (14 atm). The reaction vessel was cooled to −60° C. and CO$_2$ (78 atm) was introduced. The mixture was allowed to stir at 120° C. and 100 atm for 48 h. The autoclave was cooled to 0° C. and all the gasses were carefully released. The GC and NMR analyses indicated the complete conversion of isoprene, and formation of 3-methylpent-3-en-1-al (90%) and 4-methylpent-4-en-1-al (10%).

EXAMPLE 22
Hydrocyclocarbonylation of Methyl N-(tert-butoxycarbonyl)allylglycinate in scCO$_2$.

To a 300 mL stainless steel autoclave with two sapphire windows containing Rh(acac)(CO)$_2$ (1.5 mg, 6×10$^{-3}$ mmol)

and a diphosphite ligand, BIPHEPHOS or MCP-1, (1.2× $10^{-2}$ mmol) was added methyl N-(tert-butoxycarbonyl) allylglycinate (138 mg, 0.6 mmol). The air was replaced by CO and CO (7 atm) was introduced followed by $H_2$ (7 atm). The reaction vessel was cooled to −60° C. and $CO_2$ (85 atm) was introduced. The mixture was allowed to stir at 65° C. and 100 atm for 24 h. The autoclave was cooled to 0° C. and all the gasses were carefully released. The reaction mixture was then concentrated under vacuum and the residue was chromatographed on silica gel using hexane/AcOEt as the eluant to give methyl 1-(tert-butoxycarbonyl)-5,6-dehydropipecolate in nearly quantitative yield: Colorless oil; $[\alpha]_D^{20}$ 20.22 (c 1.83, $CHCl_3$); $^1H$ NMR ($CDCl_3$) (two rotamers) δ [1.43 (s),1.48 (s)] (9 H), 1.85–1.97 (m, 3 H), 2.28–2.34 (m, 1 H), [3.70 (s), 3.71 (s)] (3 H), [4.72 (br s), 4.76–4.80 (m), 4.89 (br s)] (2 H), [6.77 (d, J=8.6 Hz), 6.89 (d, J=8.3 Hz)] (1 H); $^{13}C$ NMR ($CDCl_3$) δ [18.26, 18.51], [23.44, 23.60], [28.12, 28.20], [52.19, 52.28], [53.07, 54.31], [81.11, 81.30], [104.14, 104.57], [124.37, 124.85], [152.21, 152.37], [171.52, 171.95]; IR (neat, $cm^{-1}$) 2977, 2846, 1753, 1712, 1655, 1371, 1313, 1168. HRMS Calcd. for $C_{12}H_{19}NO_4$: 241.1314. Found: 241.1311.

EXAMPLE 23

Preparation of 4-(tert-butoxycarbonylamino)-1,6-heptadiene

To a solution of 1,6-heptadien-4-ol (6.00 g, 53.5 mmol) in $CH_2Cl_2$ (60 mL) and pyridine (9.5 mL, 0.12 mol) was added a solution of methanesulfonyl chloride (6.2 mL, 80 mmol) in $CH_2Cl_2$ (60 mL) at 0° C. under $N_2$. After addition was complete, the reaction mixture was gradually warmed to room temperature and stirred for 20 h. Water was then added and the resulting two phases were separated. The aqueous phase was extracted with ether and the organic extracts were combined, washed with water, 2 N HCl, water, brine, dried over $MgSO_4$ and concentrated on a rotary evaporator. The residual pale yellow oil was subjected to column chromatography on silica gel using pentane/$Et_2O$ (3/2) as the eluant to give the mesylate of 1,6-heptadien-4-ol (10.1 g; 100%) as a colorless oil.

To a solution of the mesylate (10.5 g, 55 mmol) in DMF (100 mL) was added sodium azide (17.5 g, 0.27 mol) and the reaction mixture was heated at 65–75° C. for 3 h. The reaction mixture was cooled to room temperature and ether (100 mL) was added. The ether solution was washed with water five times to remove DMF. The organic phase was separated and dried over $MgSO_4$ and the solvent was removed on a rotary evaporator to afford 4-azido-1,6-heptadiene as a yellow oil (7.4 g; 98%): $^1H$ NMR ($CDCl_3$) δ 2.27–2.34 (m, 4 H), 3.43 (dddd, J=13.2, 7.05, 7.05, 5.7 Hz, 1 H), 5.11–5.19 (m, 4 H), 5.82 (ddt, J=17.1, 10.2, 7.2 Hz, 2 H).

To a solution of 4-azido-1,6-heptadiene (3.28 g, 23.9 mmol), thus obtained, in THF (50 mL) was added triphenylphosphine (7.97 g, 30.4 mmol) in portions at room temperature under nitrogen. The reaction mixture was allowed to stir at room temperature for 2 h. Water (4.5 mL) was added and the mixture was heated to reflux for 6 h. The reaction mixture was gradually cooled to room temperature and concentrated. Ethyl acetate (50 mL) was added followed by a saturated aqueous solution of $NaHCO_3$ (45 mL) and di(t-butyl) dicarbonate (7.8 g, 36 mmol). The reaction mixture was allowed to stir at room temperature for 14 h. The two phases were separated and the organic phase was washed with brine, dried over $MgSO_4$ and concentrated under vacuum to give an oily residue. The residue was subjected to column chromatography on silica gel using hexane/AcOEt (10/1) to afford 4-(t-butoxycarbonylamino)-1,6-heptadiene (3.24 g; 64%) as a pale yellow oil: $^1H$ NMR ($CDCl_3$) δ 1.34 (s, 9 H), 2.03–2.22 (m, 4 H), 3.62 (br s, 1 H), 4.43 (br s, 1 H), 4.98 (d, J=11.6 Hz, 2 H), 4.99 (d, J=15.4 Hz, 2 H), 5.60–5.77 (m, 2 H); $^{13}C$ NMR ($CDCl_3$) δ 27.30, 27.97, 38.65, 49.49. 117.55, 134.37; IR (neat, $cm^{-1}$) 3300, 2979, 2933.56, 1811.05, 1701.12, 1516.92, 1369.38. 1213.15, 1173.62. 1072.36. HRMS (CI) calcd for $C_{12}H_{21}NO_2$ ($[MH]^+$): 212.1650. Found: 212.1648.

EXAMPLE 24

Hydrocyclocarbonylation of 4-(tert-butoxycarbonylamino)-1,6-heptadiene in $scCO_2$.

To a 300 mL stainless steel autoclave with two sapphire windows containing Rh(acac)(CO)$_2$ (1.5 mg, 6×10$^{-3}$ mmol) and a diphosphite ligand. BIPHEPHOS, MCP-1 or MCP-2, (1.2×10$^{-2}$ mmol) was added 4-(tert-butoxycarbonylamino)-1,6-heptadiene (127 mg, 0.6 mmol). The air was replaced by CO and CO (7 atm) was introduced followed by $H_2$ (7 atm). The reaction vessel was cooled to −60° C. and $CO_2$ (85 atm) was introduced. The mixture was allowed to stir at 65° C. and 100 atm overnight. The autoclave was cooled to 0° C. and all the gasses were carefully released. The reaction mixture was then concentrated under vacuum and the residue was chromatographed on silica gel using hexane/AcOEt as the eluant to give 1-tert-butoxycarbonyl-2-(3-formylpropyl)-5,6-didehydropiperidine in virtually quantitative yield: Colorless oil; $^1H$ NMR ($CDCl_3$) (two rotamers) δ 1.39–1.77 (m, 17 H), 1.89–2.06 (m, 2 H), 2.47 (br s, 2 H), [4.15 (br s), 4.29 (br s)] (1 H), [4.77 (br s), 4.86 (br s)] (1 H), [6.64 (br d, J=7.8 Hz), 6.78 (br s)], (1 H), 9.76 (s, 1 H); $^{13}C$ NMR ($CDCl_3$) δ 17.51, 29.97–30.52, 43.67, [48.91, 50.29], 80.49, [104.73, 105.20], [124.06, 124.08], 202.51; IR (neat, $cm^{-1}$) 2931, 1723, 1697, 1651, 1409, 1361, 1171, 1116. HRMS (CI) calcd for $C_{14}H_{23}NO_4$ ($[MH]^+$): 254.1756. Found: 254.1760.

EXAMPLE 25

Hydrocyclocarbonylation of 1,6-heptadien-4-ol in $scCO_2$.

To a 300 mL stainless steel autoclave with two sapphire windows containing Rh(acac)(CO)$_2$ (1.5 mg, 6×10$^{-3}$ mmol) and a diphosphite ligand, BIPHEPHOS or MCP-1, (1.2×10$^{-2}$ mmol) was added 1,6-heptadien-4-ol (112 mg, 1.0 mmol). The air was replaced by CO and CO (7 atm) was introduced followed by $H_2$ (7 atm). The reaction vessel was cooled to −60° C. and $CO_2$ (85 atm) was introduced. The mixture was allowed to stir at 65° C. and 100 atm overnight. The autoclave was cooled to 0° C. and all the gasses were carefully released. The reaction mixture was then concentrated under vacuum and the residue was chromatographed on silica gel using hexane/AcOEt as the eluant to give 6-(3-formylpropyl)-2-hydroxytetrahydropyran in nearly quantitative yield: $^1H$ NMR ($CDCl_3$) (two diastereomers) δ 1.14–2.02 (m, 10 H), 2.43 (t, J=6.8 Hz, 2 H), 3.16 (br s, 1 H), [3.36–3.44 (m), 3.88–3.96 (m)] (1 H), [4.66 (d, J=9.1 Hz), 5.26 (br s)] (1 H), 9.74 (s, 1 H); $^{13}C$ NMR ($CDCl_3$) δ [17.50, 18.04], 21.95, [30.26, 30.99], [32.55, 32.03], [35.01, 35.18], [43.13, 43.52], [72.96, 75.64], [91.36, 96.21], [201.90, 202.74]; IR (neat, $cm^{-1}$) 3420, 2942, 2867, 2723, 1724, 1458, 1440, 1412, 1390, 1352, 1184, 1116, 1066, 1035, 977.

In a 25 mL round bottomed flask was placed a solution of 6-(3-formylpropyl)-2-hydroxytetrahydropyran (153 mg, 0.89 mmol), DMAP (5 mg), and $Et_3N$ (0.4 mL) in $CH_2Cl_2$ (10 mL). The solution was cooled to 0° C., and tert-butyldimethylsilyl chloride (205 mg, 1.34 mmol) in $CH_2Cl_2$ (3 mL) was added dropwise. The reaction mixture was allowed to warm to room temperature overnight, and then the solvent was removed under reduced pressure. Ether was added and the organic layer was washed with saturated NH₄Cl twice followed by brine, dried over anhydrous magnesium sulfate, and then concentrated in vacuo. The residue was submitted to column chromatography on silica gel to afford 6-(3-formylpropyl)-2-(tert-butyldimethylsiloxy) tetrahydropyran as a clear yellow oil (206 mg, 90% yield): $^1$H NMR (CDCl₃) δ 0.09 (s, 3H), 0.10 (s, 3H), 0.89 (s, 9H), 1.19–1.73 (m, 10H), 2.43 (m, 2H), 3.34 (t, 1H, J=5.7 Hz), 4.63 (d, 1H, J=9 Hz), 9.74 (s, 1H); $^{13}$C NMR (CDCl₃) δ −4.0, 18.14, 18.41, 22.21, 25.81, 30.61, 33.83, 35.25, 43.70, 75.70, 97.26, 202.63. HRMS [CI (CH₄)] calcd for C₁₅H₂₉O₃Si: 285.1886 (M−H,)⁺. Found: 285.1890 (Δ−1.4 ppm).

We claim:

1. A process comprising subjecting at least one compound containing at least one carbon—carbon double bond or at least one carbon—carbon triple bond, hydrogen and carbon monoxide, to a hydrocarbonylation reaction in supercritical carbon dioxide, in the presence of a Group VIII transition metal catalyst precursor, and a phosphite ligand.

2. The process of claim 1 wherein the compound is selected from the group consisting of alkenes, alkynes, dienes, and mixtures thereof.

3. The process of claim 2 wherein the compound is unsubstituted or contains one or more nonreactive substituents.

4. The process of claim 1 wherein the Group VIII transition metal catalyst precursor is a hydride, a halide, an organic salt, an inorganic salt, an oxide, a carbonyl compound, an amine compound, an olefin-coordinated compound, a phosphine-coordinated compound or a phosphite-coordinated compound of Group VIII transition metal.

5. The process of claim 1 wherein the phosphite ligand is selected from the group consisting of the following formulae (I) to (IV):

P(OR¹)(OR²)(OR³)   (I)

   (I-1)

(R¹O)(R²O)P-O-A-O-P(OR³)(OR⁴)   (II)

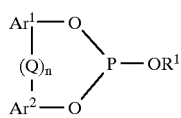   (II-1)

   (II-2)

(R¹O)(R²O)P-O-A-O-P(R³)(R⁴)   (III)

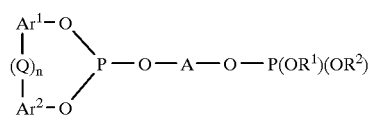   (III-1)

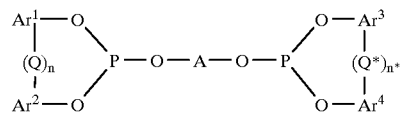   (III-2)

(R¹O)(R²O)P-O-A-P(R³)(R⁴)   (IV)

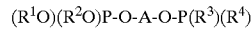   (IV-1)

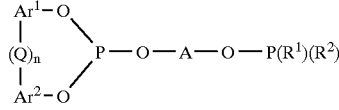   (IV-2)

wherein each R¹, R², R³ or R⁴ independently represents a C1–20 linear, branched or cyclic alkyl group, a C6–C20 aryl group or a C3–C20 heteroaromatic group, said alkyl, aryl, or heteroaromatic group being unsubstituted, or substituted with one or more groups selected from the group consisting of a C1–C20 linear or branched alkyl group, a cycloalkyl group, an alkoxy group, an aryl group, an aryloxy group, an aralkyl group, an ester group, a perfluoroalkyl group, an amide group, trialkylsilyl group and a halogen atom;

each Ar¹, Ar², Ar³ or Ar⁴ independently represents a non-substituted or substituted arylene group;

each Q or Q* independently represents a —CR⁵R⁶, —O—, —S—, —NR⁷, —SiR⁸R⁹ or —CO— group as a linker group wherein each R⁵ to R⁹ independently represents a hydrogen atom, C1–C12 alkyl group or aryl group;

each n or n* independently represents 0 or 1;

A represents a C2–C12 linear, branched or cyclic alkylene group, a C6–10 arylene group or a C12–C20 bisarylene group, said alkylene, arylene or bisarylene group being unsubstituted, or substituted with one or more groups selected from the group consisting of a C1–C20 linear or branched alkyl group, a cycloalkyl group, an alkoxy group, an aryl group, an aryloxy group, an aralkyl group, a nitro group, a cyano group, an ester group, a perfluoroalkyl group, an amide group, trialkylsilyl group and a halogen atom.

6. The process of claim 2 wherein said alkenes are selected from the group consisting of 1-alkenes and internal alkenes; said alkynes are selected from the group consisting of 1-alkynes and internal alkynes; wherein said internal alkenes, internal alkynes and said dienes are acyclic or cyclic, wherein said alkenes, alkynes, and dienes are linear or branched, and wherein said alkenes, alkynes, and dienes are unsubstituted or substituted with one or more substituents, with the proviso that said substituents are incapable of preventing the hydrocarbonylation reaction.

7. The process of claim 3 wherein the nonreactive substituent is selected from the group consisting of hydroxy, alkoxy, aryloxy, formyl, oxo, hydroxycarbonyl, amino, amido, imido, carbamoyl, ureido, cyano, nitro, alkoxycarbonyloxy, aryloxycarbonyloxy, mercapto, alkylthio, arylthio, thioxo, hydroxy(thiocarbonyl), mercaptocarbonyl, mercapto(thiocarbonyl), sulfinyl, sulfonyl, phosphino, (phosphino)oxy, phosphoryl, phosphonamido, phosphonthioamido, trisubstituted silyl, trisubstituted stannyl, and disubstituted boryl.

8. The process of claim 3 wherein the compound is an alkene selected from the group consisting of straight chain or branched 1-alkene of 2–20 carbons, straight chain or branched internal alkenes of 4–20 carbons, cycloalkenes of 3–20 carbons, unsubstituted or substituted alkenylarenes of 8–30 carbons, unsubstituted or substituted alkenylheteroaromatic compounds of 5–30 carbons, unsubstituted or substituted alkenylcycloalkanes of 5–30 carbons, unsubstituted or substituted alkenylcyclic compounds including one or more nitrogen atoms of 4–30 carbons, unsubstituted or substituted alkenylcyclic compounds including one or more oxygen atoms of 4–30 carbons, unsubstituted or substituted alkenylcyclic compounds including one or more sulfur atoms of 4–30 carbons, and unsubstituted or substituted alkenylcyclic compounds including one or more phosphorus atoms of 4–30 carbons.

9. The process of claim 3 wherein the compound is a substituted alkene selected from the group consisting of unsubstituted and substituted allylic amines, unsubstituted and substituted allylic amides, unsubstituted and substituted allylic carbamates, unsubstituted and substituted allylic sulfonamides, unsubstituted and substituted allylic phosphonamides, unsubstituted and substituted 3-butenylamides, unsubstituted and substituted 3-butenylamides, unsubstituted and substituted 3-butenylcarbamates, unsubstituted and substituted 3-butenylsulfonamides, unsubstituted and substituted 3-butenylphosphonamides, unsubstituted and substituted 4-pentenylamines, unsubstituted and substituted 4-pentenylamides, unsubstituted and substituted 4-pentenylcarbamates, unsubstituted and substituted 4-pentenylsulfonamides, and unsubstituted and substituted 4-pentenylphosphonamides.

10. The process of claim 3 wherein the compound is a substituted diene selected from the group consisting of unsubstituted and substituted 3-amino-1,4-pentadiene, unsubstituted and substituted 3-amino-1,5-hexadiene, unsubstituted and substituted 3-amino-1,6-heptadiene, unsubstituted and substituted 4-amino-1,6-heptadiene, unsubstituted and substituted 4-amino-1,7-octadiene, 5-amino-1,8-nonadiene, unsubstituted and substituted 3-hydroxy-1,4-pentadiene, unsubstituted and substituted 3-hydroxy-1,5-hexadiene, unsubstituted and substituted 3-hydroxy-1,6-heptadiene, unsubstituted and substituted 4-hydroxy-1,6-heptadiene, unsubstituted and substituted 4-hydroxy-1,7-octadiene, 5-hydroxy-1,8-nonadiene, unsubstituted and substituted 3-mercapto-1,4-pentadiene unsubstituted and substituted 3-mercapto-1,5-hexadiene, unsubstituted and substituted 3-mercapto-1,6-heptadiene, unsubstituted and substituted 4-mercapto-1,6-heptadiene, unsubstituted and substitute mercapto-1,7-octadiene, 5-mercapto-1,8-nonadiene.

11. The process of claim 1 wherein the Group VIII transition metal is selected from the group consisting of rhodium, platinum, ruthenium, cobalt, iridium, osmium, and palladium.

12. The process of claim 1 wherein the Group VIII transition metal is rhodium.

13. The process of claim 12 wherein the rhodium catalyst precursor is selected from the group consisting of rhodium trichloride, rhodium nitrate, rhodium acetate, rhodium oxide, acetylacetonatorhodium dicarbonyl, bis(chlororhodium dicarbonyl), bis[chloro(cyclooctadiene) rhodium], bis[chloro(norbornadiene)rhodium], bis[chloro (cyclohexadiene)rhodium], bis[chloro-bis(ethylene) rhodium], bis[($\mu$-tert-butylthio)rhodium dicarbonyl], hydridorhodium carbonyl tristriphenylphosphine, chlororhodium tris(triphenylphosphine), tetrarhodium dodecacarbonyl, hexarhodium hexadecacarbonyl, and dirhodium tetraacetate.

14. The process of claim 1 where in the phosphite ligand is selected from the group consisting of 3,3',5,5'-tetra-(1,1-dimethylethyl)-2,2'-bis[bis[(2-naphthyloxy)phosphino]oxy] biphenyl (MCP-1), 3,3',5,5'-tetra-(1,1-dimethylethyl)-6,6'-dimethyl-2,2'-bis[bis[(1-naphthyloxy)phosphino]oxy] biphenyl (MCP-2), O,O'-[[3,3'-bis(1,1-dimethylethyl)-5,5'-dimethoxy[1,1'-biphenyl]-2,2'-diyl]bis(oxy)]bisdibenzo[d, f][1,3,2]dioxaphosphepin (BIPHEPHOS), and 4-[[2'-(diphenylphoshino)[1,1'-binaphthalen]-2-yl]oxy]dinaphtho [2,1-d:1',2'-f][1,3,2]dioxaphosphepin (BINAPHOS).

15. The process of claim 1 wherein the reaction temperature is in a range of about 31–150° C.

16. The process of claim 15 wherein the reaction temperature is in a range of about 35–80° C.

17. The process claim 1 wherein the reaction is carried out at a total pressure in a range of about 75–200 atm.

18. The process of claim 1 wherein the concentration of the catalyst precursor is in a range of $1 \times 10^{-9}$ M to $1 \times 10^{-3}$ M, as calculated as the metal.

19. The process of claim 18 wherein the concentration of the catalyst precursor is in a range of $1 \times 10^{-8}$ M to $1 \times 10^{-4}$ M, as calculated as the metal.

20. The process of claim 12 wherein the concentration of the catalyst precursor is in a range of $1 \times 10^{-9}$ M to $1 \times 10^{-3}$ M, as calculated as rhodium metal.

21. The process of claim 20 wherein the concentration of the catalyst precursor is in a range of $1 \times 10^{-8}$ M to $1 \times 10^{-5}$ M, as calculated as rhodium metal.

22. The process of claim 1 wherein the partial pressure of carbon monoxide is about 1–100 atm and the partial pressure of hydrogen is about 1–100 atm.

23. The process of claim 22 wherein the partial pressure of carbon monoxide is about 1–50 atm and the partial pressure of hydrogen is about 1–50 atm.

24. The process of claim 1 wherein the ratio of hydrogen to carbon monoxide is about 1–10 to 10:1.

25. The process of claim 24 wherein the ratio of hydrogen to carbon monoxide is about 1:5 to 5:1.

26. The process of claim 5 wherein the phosphite ligand has formula (I).

27. The process of claim 5 wherein the phosphite ligand has formula (I-1).

28. The process of claim 5 wherein the phosphite ligand has formula (II).

29. The process of claim 5 wherein the phosphite ligand has formula (II-1).

30. The process of claim 5 wherein the phosphite ligand has formula (II-2).

31. The process of claim 5 wherein the phosphite ligand has formula (III).

32. The process of claim 5 wherein the phosphite ligand has formula (III-1).

33. The process of claim 5 wherein the phosphite ligand has formula (III-2).

34. The process of claim 5 wherein the phosphite ligand has formula (IV-1).

35. The process of claim 5 wherein the phosphite ligand has formula (IV-2).

* * * * *